(12) United States Patent
Maier et al.

(10) Patent No.: US 11,747,422 B2
(45) Date of Patent: Sep. 5, 2023

(54) METHOD FOR OPTIMIZED BIAS AND SIGNAL INFERENCE IN MAGNETIC RESONANCE IMAGE ANALYSIS

(71) Applicant: Stephan Maier, Askim (SE)

(72) Inventors: Stephan Maier, Askim (SE); Stefan Kuczera, Pixbo (SE)

(73) Assignee: Stephan Maier, Askim (SE)

( * ) Notice: Subject to any disclaimer, the term of this patent is extended or adjusted under 35 U.S.C. 154(b) by 25 days.

(21) Appl. No.: 17/504,129

(22) Filed: Oct. 18, 2021

(65) Prior Publication Data

US 2022/0034985 A1 Feb. 3, 2022

Related U.S. Application Data

(63) Continuation of application No. PCT/EP2019/060686, filed on Apr. 25, 2019.

(30) Foreign Application Priority Data

Apr. 16, 2019 (EP) ..................................... 19169433

(51) Int. Cl.
*G01R 33/563* (2006.01)
*A61B 5/055* (2006.01)
*G01R 33/50* (2006.01)
*G01R 33/56* (2006.01)

(52) U.S. Cl.
CPC ........ *G01R 33/56341* (2013.01); *A61B 5/055* (2013.01); *G01R 33/50* (2013.01); *G01R 33/5602* (2013.01); *G01R 33/5608* (2013.01)

(58) Field of Classification Search
None
See application file for complete search history.

(56) References Cited

U.S. PATENT DOCUMENTS 5,786,692 A 7/1998 Maier et al.
6,751,495 B2 * 6/2004 Maier .................... G01R 33/56
324/307

OTHER PUBLICATIONS

Pruessmann, Klass P., et al., "SENSE: Sensitivity Encoding for Fast MRI", Magnetic Resonance in Medicine, 1999, pp. 952-962, vol. 42. (pp. 11).

(Continued)

*Primary Examiner* — Rodney E Fuller
(74) *Attorney, Agent, or Firm* — BUCHANAN, INGERSOLL & ROONEY PC

(57) ABSTRACT

An approach to estimate noise, Rician signal bias and true signal in magnitude signal data obtained with magnetic resonance imaging. The method uses multiple measurements at different scan parameter settings, also referred to as weightings, and an iterative algorithm to estimate noise, expected signal and associated Rician signal bias. Measurements at all measured weighting levels contribute to the ultimate estimation of the bias-free signal decay function. Therefore, of the so processed magnetic resonance image data, weighted signals can be computed at arbitrary weighting levels and with considerably better signal-to-noise ratio than the originally obtained data at corresponding weightings. Bias-free weighted image data at desired weighting levels, maps of the decay function fit parameters, or maps of a combination of such decay function parameters can be used for rapid and highly sensitive tissue characterization.

17 Claims, 15 Drawing Sheets

(56) References Cited

OTHER PUBLICATIONS

Turner, Robert, PhD, et al., "Echo-Planar imaging of Intravoxel Incoherent Motion", Radiology, Nov. 1990, pp. 407-414, vol. 177, No. 2, Wiley-Liss, Inc. (8 pages).

Alipoor, Mohammad, et al., "Noise Estimation and Bias Correction of diffusion Signal Decays: Application to Prostate Diffusion Imaging", Apr. 26, 2019, vol. 27, 3404, XP040710790, Proc. International Society for Magnetic Resonance in Medicine. (4 pages).

Bai, Ruiliang, et al., "A framework for accurate determination of the T2 distribution from multiple echo magnitude MRI images", Journal of Magnetic Resonance, May 4, 2014, pp. 53-63, vol. 244, XP028854902, Elsevier, Inc. (11 pages).

International Search Report (PCT/ISA/210) and Written Opinion (PCT/ISA/237) dated Jun. 24, 2020, by the European Patent Office as the International Searching Authority for International Application No. PCT/EP2019/060686.

Koay, Cheng Guan, et al., "Analytically exact correction scheme for signal extraction from noisy magnitude MR signals", Journal of Magnetic Resonance, Feb. 20, 2006, pp. 317-322, vol. 179, No. 2, XP024919576, Elsevier, Inc. (6 pages).

Kristoffersen, Anders, "Optimal estimation of the diffusion coefficient from non-averaged and averaged noisy magnitude data", Journal of Magnetic Resonance, Jul. 18, 2007, pp. 293-305, vol. 187, No. 2, XP022164771, Elsevier, Inc. (13 pages).

Langkilde Fredrik et al., "Evaluation of Fitting Models for Prostate Tissue Characterization Using Extended-Range b-Factor Diffusion-Weighted Imaging", Magnetic Resonance in Medicine, Jul. 18, 2007, pp. 293-305, vol. 187, No. 2, XP022164771, International Society for Magnetic Resonance in Medicine. (13 pages).

\* cited by examiner

METHOD FOR OPTIMIZED BIAS AND SIGNAL INFERENCE IN MAGNETIC RESONANCE IMAGE ANALYSIS

BACKGROUND

1. Field of Invention

The invention generally relates to methods for obtaining, processing and displaying pathologically significant images and parameter maps associated with magnitude signals measured in magnetic resonance imaging experiments. More particularly, the invention relates to methods for obtaining and processing magnitude signals from a magnetic resonance imaging apparatus, where the signal decay or recovery is related to an underlying physical process, such as Brownian motion, T1 relaxation, T2 relaxation or T2* relaxation, and use of the so processed magnetic resonance output signals to generate bias-free magnitude images with superior signal-to-noise ratio, as well as parameter maps, to visualize internal body tissue(s).

2. Summary of the Prior Art

Tissue differentiation, localization and characterization always have been basic goals of magnetic resonance imaging. Indeed, the desire to distinguish between normal tissue and tumor tissue using magnetic resonance imaging techniques was recognized several decades ago. At that time, it was realized that the spin-lattice, so-called "T1", as well as the spin-spin, so called "T2", relaxation parameters are different between normal and cancerous tissue. Accordingly, by appropriately mapping the various T1 and/or T2 relaxation times determined from magnetic resonance signal of various voxels in an anatomical slice of interest as relative image amplitudes, it was possible to create images generally showing the demarcation of tumor tissue from adjacent normal tissue. More recently, mapping of the faster "T2*" relaxation parameter with so called gradient echo sequences has been proposed to measure tissue iron content and levels of deoxygenated hemoglobin. The observed signal recovery related to T1 relaxation, and signal decay related to T2 or T2* relaxation can be described with multi-exponential functions. Yet another important method that relies on the quantification of multi-exponential signal decays is magnetic resonance diffusion-weighted imaging, which can be used to visualize the Brownian motion of molecules in tissues. In this regard, so-called "apparent diffusion coefficient" (ADC) maps, as a quantitative measure of the diffusion-related signal decay, can provide useful information about the presence of acute stroke, fluid-filled cysts or tumor lesions.

In the intervening time period, methods of obtaining T1, T2, T2* or diffusion-weighted images and related maps using magnetic resonance imaging techniques have vastly improved. In addition, a large amount of experience has been gained in the in vivo application of these methods and the added use of contrast agents has resulted in even better diagnostic possibilities. In fact, methodology has evolved to the point that the demarcation of tissue boundaries is considered to be basically conventional. Nevertheless, the determination of tissue or tumor margins using this "conventional" methodology is not entirely successful.

The most widespread clinical and research use of quantitative signal analysis in magnetic resonance occurs in the context of diffusion imaging. It is also the area, where understanding the observed signal decays requires the most complex models and where a directional dependence plays a role. But many aspects of the problems that can arise in the analysis of such signal decays, are equally applicable to T1, T2, or T2* relaxation mapping. To better understand the analysis concepts involved, it will be instructive to first generally discuss some basics, such as the acquisition of diffusion-weighted signals with magnetic resonance imaging and how the measured signal decays relate to the tissue under observation. First, the concepts of isotropic diffusion, the so-called "diffusion coefficient", and the measurement of the "diffusion coefficient" with magnetic resonance will be presented in a generalized manner. Second, the concepts of the extension of the definition of diffusion to so-called "anisotropic" diffusion, and the characterization of diffusion with a diffusion tensor, rather than a single coefficient, will be presented. Third, the effects of having multiple compartments with different diffusion properties within a detected voxel signal, such as the combined effect of blood perfusion in the micro-circulatory system and water diffusion in the surrounding tissue. Finally, the phenomenon of a departure from the normally adopted magnetic resonance signal behavior when the diffusion encoding range is extended substantially and, therefore, signal-to-noise ratios tend to be low, will lead to a discussion of the present invention.

First, with regard to isotropic diffusion and its measurement using magnetic resonance, it will be recognized that in a pure liquid such as water at room temperature, the individual water molecules are in constant motion due to the phenomenon of thermal agitation. This phenomenon is commonly referred to as "Brownian motion". The so-called "diffusion coefficient" (herein sometimes referred to as "D") is a measure of this molecular motion, and it can be determined with magnetic resonance techniques.

More particularly, a magnetic field gradient can be used to "tag" atomic level spins in a sample according to their location in space at the time of the application of a first magnetic gradient to the sample. A second gradient, applied at a later time, then serves to probe how far, on average, the individual spins have moved between the time of the first gradient application and the time of the second gradient application. In the ideal case, these magnetic field gradients are applied in brief, strong bursts separated by a common well-defined time period. In practice in clinical magnetic resonance systems, however, the gradients are applied for a moderate duration of several milliseconds or several tens of milliseconds, and the leading edges of the respective bursts are separated by delays of similar, but slightly longer duration.

Under these conditions, the diffusion encoding level, i.e., the so-called "b-factor", is defined by the following relationship:

$$b = \gamma^2 G^2 \delta^2 (\Delta - \delta/3)$$

Where $\gamma$ is the gyromagnetic ratio (42.58 MHz/Tesla for protons), G is the magnetic field gradient amplitude, $\delta$ is the duration of each gradient lobe, and $\Delta$ is the separation between the leading edges of the lobes. Thus, with one gradient pulse placed prior to and the other following the 180° radio frequency (RF) inversion pulse of a spin echo sequence (90° RF slice select—TE/2-180° RF inversion—TE/2-signal acquisition), the signal S of the spin-echo measured at echo time TE for isotropic diffusion is given by the mono-exponential relationship:

$$S(b) = S_0 \exp(-bD).$$

In this relationship, $S_0$ depends upon machine constants, the spin-spin relaxation time T2, the spin-lattice relaxation time T1 in any experiment that repeats measurements every repetition time period TR, and the spin density $\rho$. Specifically, the diffusion coefficient D may be measured by making multiple measurements of S as a function of b, plotting the natural logarithm of S vs. b and then performing a linear regression whose slope provides the experimental measurement of D. Alternatively and preferably, a non-linear least-square regression analysis can be used to directly infer the fitting exponential function without performing the logarithm operation. The value of b is most conveniently varied by keeping the gradient timings fixed and incrementing the amplitude G of the magnetic field gradient.

As will be seen from FIG. 1, the logarithmic decay of signal intensity from neat solutions of water as a function of b measured on a clinical scanner follows a straight-line. This is indicative of mono-exponential decay above the base line noise level. The actual diffusion coefficient measured from the slope of the decay shown above the base line noise values is in excellent agreement with published literature values. Hence, for isotropic diffusion in neat liquids, it may be said that the logarithm of the intensity of the magnetic resonance signal varies linearly with b above a given noise threshold.

Second, the extension of the foregoing concepts to the measurement of tissue water diffusion within the context of magnetic resonance imaging led to certain adjustments in the above-stated theory. Thus, it was quickly realized that in certain organs like the brain, preferred directions of water diffusion exist. More particularly, diffusion along one direction, as selected by the direction of the magnetic field gradient vector could be different than the diffusion along another direction. In the brain, this lack of isotropy of the diffusion coefficient (the so-called "diffusion anisotropy") was, and is, attributed to the presence of nerve fiber tracts along which water is more free to move than it is in direction perpendicular to these tracts.

Accordingly, there is reason to believe that tissue water diffusion cannot be characterized with a single diffusion coefficient D, as for neat liquids. Instead, tissue water diffusion apparently requires a more complex formalism in order to characterize it accurately. This more complex formalism has been found to be presentable using the concept of a diffusion tensor.

A 3×3 matrix may represent the diffusion tensor. This may be accomplished with six independent elements. Indeed, in the light of the phenomenon of restricted or anisotropic diffusion, it generally is agreed in the art that at least three orthogonal directions of the diffusion sensitization gradient (which are independent of the preferred directional diffusion) should be sampled to generate trace images, i.e., maps of a rotationally invariant measure of diffusion. These trace images are the sum of the diagonal elements of the diffusion tensor. Further, a minimum of six directions must be sampled for each voxel, if the full diffusion tensor is to be evaluated for potentially useful studies related to fiber architecture. Even more advanced acquisition protocols and analysis formalism have been developed to detect the presence of crossing fibers.

Thus, the current trend in the clinical implementation of diffusion imaging is to sample multiple slices of the brain, each at a low and a high b-factor, the latter being typically on the order of about 1000 sec/mm². This high b-factor sampling commonly is repeated for three orthogonal diffusion sensitizing gradient directions, if only a rotationally invariant measure of diffusion is needed, or at least six non-collinear and non-coplanar diffusion sensitizing gradient directions, if the assessment of diffusion anisotropy and preferred direction of diffusion is planned. Nevertheless, despite additional complexity added by the diffusion tensor formalism, the logarithmic plot of signal versus b-factor along a selected diffusion sensitizing direction is still seen to follow a substantially mono-exponential best-fit relationship.

Still other experiments, however, have suggested that the mono-exponential signal decay vs. b-factor relationship just mentioned may not be necessarily accurate. Thus in vivo studies of water diffusion in brain, liver and prostate have suggested that the signal decay variation with b-factor is a bi-exponential function over a limited b-factor range under 500 sec/mm².

Although the departure from a simple mono-exponential decay was found to be small, it is generally considered to be attributable to perfusing blood. More specifically, blood in the micro-circulation has a very high diffusion coefficient that is not attributable to the normal, thermal Brownian motion associated with the remainder of the tissue water (i.e., water within and between the cells, but not in the vasculature). Consequently, there is a general consensus that there is indeed a small, very quickly diffusing component contributing to signal decay at low b-factors under 300 sec/mm² in blood perfused organs. Diffusion coefficients determined by signal sampling at different b-factors between 0 and 1000 sec/mm², therefore, are currently usually referred to as "apparent diffusion coefficients" (ADC) rather than more generically as diffusion coefficients D.

To minimize the effect of perfusion on the measured diffusion coefficient, routine clinical magnetic resonance diffusion imaging is conducted at b-factors of between about 100 and 1000 sec/mm². Average ADC maps are then generated on a pixel-by-pixel basis assuming that the "best-fit" relationship between the magnetic resonance signal and the b-factor is a mono-exponential function (substantially as set forth above with regard to isotropic diffusion).

Still more recently, experiments conducted at higher b-factors (up to maximum b-factors between 2000 and 10,000 sec/mm², i.e., two to ten times the maximum b-factor used in the most conventional clinical applications) revealed also a departure from a simple mono-exponential decay. The nature of this deviation is independent from the perfusion effect observed at low b-factors and can be separated by not acquiring signals at low b-factors up to 300 sec/mm² or ignoring these values in the analysis.

As will be seen from FIG. 2, with such an extended b-factor measurement range, the signal at higher b-factors is higher as one might predict by looking only at signals obtained up to a b-factor of 1000 sec/mm² and then extrapolating to higher b-factors with a mono-exponential function. It is generally agreed upon that the observed departure from a mono-exponential decay over this extended decay stems from the presence of different diffusion environments within an image voxel. One obvious cause can be a partial volume effect from a voxel containing both tissue and liquid, e.g., a voxel where tissue borders to cystic fluid. The diffusion within the cyst would be similar as in a neat solution of water at body temperature, but higher than in the adjacent tissue. Such partial volume contributions of liquid pools can be eliminated with a suitable sequence of excitation pulses that exploit differences in T1 relaxation. With such preparation, signal decays are comparable to voxels with uniform tissue content, but still exhibit clearly non-mono-exponential signal decay. The consensus is that in tissues at least two compartments can be differentiated, i.e., an extra-cellular compartment with hindered diffusion and an intra-cellular compartment restricted by the cell membrane.

Accordingly, signal decay models have been proposed that account for the presence of more than one diffusion compartment. One of the simplest models that describe a non-mono-exponential diffusion signal decay and which also reflects the nature of two compartments is the bi-exponential model:

$$S(b)=S_0(f \cdot \exp(-bD_f)+(1-f) \cdot \exp(-bD_s))$$

This model is derived from the mono-exponential equation discussed above in connection with isotropic diffusion. In this equation, $D_f$ and $D_s$ describe the diffusion coefficients of two compartments with fast and slow diffusion, respectively. The fraction $f$ is used to account for the relative signal contribution of each compartment.

While this model has been highly successful to describe the observed tissue water signal decay at higher b-factors in different tissues, e.g., the extra and intra-axonal diffusion orthogonal to nerve fibers, it may not be sufficient to fully describe the observed signal decay. It has been suggested that diffusion within the cells is also compartmentalized, e.g., by organelles, such as the nucleus, mitochondria and vesicles, which are known to be surrounded by membranes that impede the water exchange with their surroundings. One obvious extension of the bi-exponential model would be to add one or even more compartments, each characterized by a different diffusion coefficient. However, it was soon realized that the prevailing noise in typical data would usually not permit the finding of stable numerical solutions for more than two compartments. An inverse Laplace transform of the measured decay signal would be the mathematical method to systematically decompose the multi-exponential signal decay into different components, each with a specific mono-exponential decay. However, such approach would not be practical below signal-to-noise ratios of at least 1000:1 (whereby signal-to-noise ratio refers to the signal-to-noise ratio of the image with the lowest diffusion weighting), a level that is at least off by a magnitude from what is observed in typical clinical exams.

Nevertheless, in order to account for a multitude of compartments with different diffusion coefficients, it was then suggested to employ fits that rely on a continuous distribution of coefficients. A gamma distribution of diffusion coefficients, characterized by the shape parameter k and the scaling parameter $\theta$ results in the following particularly simple relationship for the signal decay without any exponential function:

$$S(b) = \frac{S_0}{(1+\theta b)^k}$$

This relationship describes observed signal decays in tissues remarkably well. Another distribution of diffusion coefficients results when the signal decay relationship is described with a stretched exponential function:

$$S(b)=S_0 \exp(-(bD)^\alpha)$$

Where a stretching coefficient $\alpha$ introduces the deviation from a simple mono-exponential decay. The resulting distribution is characterized by a relatively large contribution of fast diffusion compartments, which makes it suitable to account for the perfusion effect discussed earlier.

Yet, another widely used model is based on the analysis of changes in the spin motion probability distribution. In the case of a mono-exponential decay, the spin motion probability distribution is a normal distribution. The deviation from a normal distribution is expressed by the excess kurtosis factor K and the relationship between measured signal S and b can be approximated with a Taylor expansion of the decaying exponential. It is usually truncated to a second-order polynomial in b according to the following relationship:

$$S(b) = S_0 \exp\left(-b \cdot ADC_K + b^2 \cdot ADC_K^2 \cdot \frac{K}{6}\right)$$

The variable $ADC_K$ represents the apparent kurtosis diffusion coefficient. An important advantage of the kurtosis model is the fact that $ADC_K$ equals the apparent diffusion coefficient (ADC) measured over the routine clinical range of b-factors between 100 and 1000 sec/mm$^2$. Since the Taylor expansion is truncated, the positive second order term starts to dominate at higher b-factors and, therefore, from a certain b-factor on an increase of the fitted signal, rather than decay, can be observed. To ensure that S(b) is a monotonically decreasing function of the b-factor, an upper bound $b \leq 3/(K \cdot ADC_K)$ can be derived.

Model functions like the gamma distribution related decay model, the stretched exponential model and the kurtosis model may indeed better reflect the underlying diffusion in tissues than the simple bi-exponential model. Still, for signal-to-noise ratios prevalent in clinical exams none of the models follows the observed signal decay significantly better. At signal-to-noise ratios greater than 200:1, however, it was observed for normal and cancerous prostate tissue that the gamma distribution related model and the bi-exponential model yield superior fits (see Langkilde F, Kobus T, Fedorov A, Dunne R, Tempany C, Mulkern R V, and Maier S E.; Evaluation of Fitting Models for Prostate Tissue Characterization Using Extended-Range b-Factor Diffusion-Weighted Imaging, *Magn Reson Med.* 79:2346-2358, 2018).

It was soon realized that images obtained at higher than typical diffusion-weighting, i.e., with b-factors higher than 1000 sec/mm$^2$, resulted in superior contrast between tissues and, therefore, such highly diffusion-weighted images are generally considered useful for diagnosis. As will be seen from FIG. 3, the resulting contrast can actually be minimal at an intermediate b-factor and maximal for a b-factor well above 1000 sec/mm$^2$. Particularly for the detection of prostate cancer lesions, imaging at high b-factors has proven highly beneficial and has been ubiquitously adapted by the clinical community. Initially, images were obtained with endo-rectal radio-frequency coils, which resulted in good signal-to-noise ratio even at higher b-factors, at least in the peripheral zone of the prostate, i.e., next to the coil placed in the rectum. More recently, the application of magnetic resonance imaging in prostate cancer has almost taken on the role of a screening method and there has been a clear incentive, to eliminate the invasive coil, which was a major reason for patient discomfort during the exam, patient risks and high exam costs.

To combat the vastly inferior signal-to-noise ratio that results with external coils, signal averaging and a reduction in spatial resolution is typically performed. A reduction in spatial resolution is not desirable, since partial-volume effects become more prevalent and lesions may not be equally conspicuous. On the other hand, signal averaging, the way it typically is performed, will reduce noise-related signal fluctuations across the image, but it will also introduce a signal bias, that leads to reduced contrast-noise-ratios.

Typically, signal averaging is performed with the magnitude of the signal. The reason for employing magnitude signal averaging rather than complex signal averaging are phase fluctuations in the complex signals obtained during the different measurements performed for the purpose of averaging. The phase fluctuations are the result of the very strong diffusion encoding gradients in the presence of small involuntary motion, i.e., the diffusion encoding gradient act concurrently as very strong velocity encoding gradients, which proportionally to the velocity encountered during the encoding interval change the phase of the signal.

As will be seen from FIGS. 4A and 4B, it is well known in the field of signal processing that averaging of complex signals after the application of the non-linear magnitude operation will result in a Rician signal distribution and signal bias. At signal-to-noise ratios of 3:1, the resulting bias of the signal expectation value begins to play an important role that increases with decreasing signal-to-noise ratio. The detrimental effect of this bias is not only felt during signal averaging, but also with signal decay analysis, which for the reasons outlined above also has to be performed with magnitude data. Particularly if high diffusion weighting is employed, the signal bias will impress as a compartment with very slow diffusion.

Since obtaining such highly diffusion-weighted images has become clinically very important to detect tumor lesions, imaging protocols now tend to include b-factors above 1000 sec/mm². A basic mono-exponential analysis is then performed based on all signals measured up to the highest b-factor, because ADC maps are generally considered useful to detect lesions, but even to categorize different tumors or the aggressiveness of detected cancer lesions. However, as has become clear from the foregoing, diffusion signal decays in tissues measured with b-factors higher than 1000 sec/mm² cannot be considered mono-exponential and if notwithstanding mono-exponential analysis is applied to measurements obtained over different ranges of b-factors, as will be seen from FIGS. 5A and 5B, different ADC values will result. This clearly works against the universal establishment of ADC as a measure to quantitatively categorize lesions, particularly since there are no standardized b-factor measurement ranges. As will be seen from FIG. 6, even the establishment of consistent settings for b-factors would not be successful, since b-factors will invariably vary within the imaging volume due to non-linearities of the magnetic field gradients. Also not practical with present protocols is the use of the kurtosis model with the truncated Taylor expansion of the decaying exponential to obtain a b-factor range independent $ADC_K$, since much higher than typically employed b-factors are necessary to establish reliable measures of $ADC_K$ and K.

SUMMARY OF THE INVENTION

Accordingly, it is an object of the present invention to provide magnetic resonance imaging method and apparatus for the visualization of various tissue pathologies within healthy tissue with greater definition, clarity, reliability, and protocol and system independence than has heretofore been possible.

It also is an object of the present invention to provide a method and apparatus of tissue visualization that provides well-defined, non-invasive imaging without the need for contrast agents with their related complications and cost. These and other objects and advantages of the present invention arise from the fact that it now has been shown that diffusion-weighted magnetic resonance image signals in tissues taken over a wide b-factor range in fact are best described with non-mono-exponential signal decay models, such as the bi-exponential model, the gamma-distribution related model, the stretched exponential model and the kurtosis model.

According to a first aspect of the invention, there is provided a method for highly reliable inference of signal and bias in weighted images, the weighted images being at least one of diffusion weighted, echo time weighted and repetition time weighted images, said method comprising the steps of:
  a) providing a magnetic resonance imaging apparatus capable of operation at different encoding levels;
  b) acquiring a set of magnitude signal decays from a patient using said magnetic resonance imaging apparatus at each of a selected plurality of encoding levels distributed across a range of encoding levels within its capability, each said set of signal decays being representative of an image of a preselected cross-section of the patient, and each said signal decay of each said set corresponding to a pixel of its associated image;
  c) setting or initializing the value of noise $\sigma_g$ for each pixel to 0 or a suitable very small value;
  d) processing said acquired or bias-corrected signal decays on a pixel by pixel basis to obtain the best possible fit between them and a non-mono-exponential equation wherein a non-linear least-squares method is used to obtain a fit;
  e) determining $\theta_i = \hat{s}_i / \sigma_g$ for each fitted signal $\hat{s}_i$ as an estimate for the signal-to-noise ratio at each measured signal $s_i$;
  f) obtaining for each pixel a first estimation of noise $\sigma_g$, taking into account the non-linear behavior of the noise distribution in relation to a true signal;
  g) determining for each pixel the Rician signal bias $b_i$ for each fitted signal level $\hat{s}_i$ determined in d);
  h) obtaining for each pixel a bias-corrected signal value $s_i^c$ by subtracting the Rician signal bias $b_i$ determined in g) from the measured signal level $s_i$ acquired in d);
  i) repeating steps d) to h) until the change of $s_i^c$ falls under a predefined threshold.

In an embodiment, the weighted images are diffusion-weighted images, wherein the magnetic resonance imaging apparatus is capable of operation at different diffusion encoding levels, b-factors, at least between an upper and a lower limit, said lower limit preferably being below 500 sec/mm2, and more preferably below 300 sec/mm2, and most preferably below 150 sec/mm2, such as about 100 sec/mm2 or lower, and the upper limit preferably being above 2000 sec/mm2, and more preferably above 3000 sec/mm2, and most preferably about 5000 sec/mm2 or higher.

In another embodiment, the weighted images are echo-time weighted images, wherein the magnetic resonance imaging apparatus is capable of operation at different echo time encoding levels.

In yet another embodiment, the weighted images are repetition time weighted images, wherein the magnetic resonance imaging apparatus is capable of operation at different repetition time encoding levels.

In case of diffusion-weighting, the non-mono-exponential equation in step d) above may be of the form:

$$S(b) = S_0(f \cdot \exp(-bD_f) + (1-f) \cdot \exp(-bD_s))$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density $\rho$, wherein b is the diffusion encoding level, preferably determined for each pixel location, and wherein Df is a parameter for the fast diffusion coefficient, and wherein Ds is a parameter for the slow diffusion coefficient, and wherein f is parameter for a fraction to account for the relative signal contribution of the fast and slow diffusion compartment.

The first estimation of noise $\sigma_g$ for each pixel in step f) above may be made by performing the following computation:

$$\sigma_g = \frac{1}{N_f} \sum_1^N \frac{(\hat{s}_i - s_i)^2}{2\frac{\hat{s}_i}{\theta_i} + 2\theta_i \left(\hat{s}_i - \frac{\theta_i^2}{2\hat{s}_i^2}\left(\exp\left(-\frac{\theta_i^2}{4}\right)\right)\sqrt{\frac{\pi}{2}}\frac{\hat{s}_i}{\theta_i}\right.}{\left.\left[\left(\hat{s}_i^2 + 2\frac{\hat{s}_i^2}{\theta_i^2}\right)I_0\left(\frac{\theta_i^2}{4}\right) + \hat{s}_i^2 I_1\left(\frac{\theta_i^2}{4}\right)\right]\right)}$$

wherein N equals the number of b-factors, and
wherein $N_f = N - N_p$, and
wherein $N_p$ equals the number of free fit parameters, and
wherein $\theta_i$ is an estimated signal-to-noise ratio obtained in step 1e;
wherein $\hat{s}_i$ is the best fit equation result, and
wherein $s_i$ is the measured signal.

Alternatively, the first estimation of noise $\sigma_g$ for each pixel in step f) above may be made by performing the following computation:

$$\sigma_g = \frac{1}{N_f} \sum_1^N |\hat{s}_i - s_i| / \alpha(\theta_i)$$

wherein N equals the number of b-factors, and
wherein $N_f = N - N_p$, and
wherein $N_p$ equals the number of free fit parameters, and
wherein $\alpha(\theta_i)$ is an estimated mean value of absolute noise residuals at a specific signal-to-noise ratio $\theta_i$ of a Rician signal distribution with $\sigma_g = 1$;
wherein $\hat{s}_i$ is the best fit equation result, and
wherein $s_i$ is the measured signal.

The estimation of a mean value of absolute noise residuals may comprise:
a) simulating a multitude of signal levels $\theta \geq 0$;
b) simulating for each signal level a multitude of realizations with the addition of Gaussian distributed random noise with $\sigma_g = 1$;
c) forming the magnitude of each signal so realized in step b);
d) determining for each signal level $\theta$ the absolute value of the difference between original signal obtained in step a) and each value obtained in the previous step;
e) storing the arithmetic average of these differences obtained in step d) for each signal level $\theta$ as function values of $\alpha(\theta)$;
f) determining suitable linear interpolations for $\alpha(\theta)$.

Here, after step c), a step forming arithmetic averages within groups of k such magnitude signals may be inserted.

The determining for each pixel the Rician signal bias $b_i$ for each fitted signal level $\hat{s}_i$ in step g) above may be made according to the equation:

$$b_i = \frac{1}{2\sigma_g^2}\left(\exp\left(-\frac{\hat{s}_i^2}{4\sigma_g^2}\right)\right)\sqrt{\frac{\pi}{2}}\,\sigma_g\left[(\hat{s}_i^2 + 2\sigma_g^2)I_0\left(\frac{\hat{s}_i^2}{4\sigma_g^2}\right) + \hat{s}_i^2 I_1\left(\frac{\hat{s}_i^2}{4\sigma_g^2}\right)\right] - \hat{s}_i$$

The $\sigma_g$ values determined in step f) above for different diffusion encoding directions may be:
a) averaged arithmetically on a pixel by pixel basis;
b) steps g) and h) above may be repeated with this new $\sigma_g$ value to obtain for each pixel a final set of bias-corrected signal values $s_i^c$;
c) step d) above may be repeated with these final values for $s_i^c$.

The method may further comprise:
a) the spatial maps of $\sigma_g$ values determined in step f) above are low pass filtered;
b) steps g) and h) above are repeated with this new $\sigma_g$ value to obtain for each pixel a final set of bias-corrected signal values $s_i^c$;
c) step 1d) is repeated with these final values for $s_i^c$.

In the method on a pixel by pixel basis, $s_i$ measured in b) above at the lowest encoding level, such as b-factor, may be divided with $\sigma_g$ and the result may be stored as signal-to-noise ratio map.

Arithmetic averages of parameters determined for different encoding levels, such as different diffusion encoding directions, in step d) above, may be computed.

Alternatively, or additionally, geometric averages of signals determined for different diffusion encoding directions, in step d) above may be computed.

In case of diffusion weighting, step d) above may be accomplished by processing said acquired or bias-corrected signal decays on a pixel by pixel basis to obtain the best possible fit between them and a non-mono-exponential equation of the form:

$$S(b) = \frac{S_0}{(1 + \theta b)^k}$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density $\rho$, wherein b is the diffusion encoding level, preferably determined for each pixel location, and wherein k is a shape parameter of a gamma distribution that is associated with this function, and wherein $\theta$ is a scaling parameter of a gamma distribution that is associated
with this function, and wherein a non-linear least-squares method is used to obtain a fit.

Alternatively, in the case of diffusion-weighting, step d) above may be accomplished by processing said acquired or bias-corrected signal decays on a pixel by pixel basis to obtain the best possible fit between them and a non-mono-exponential equation of the form:

$$S(b) = S_0 \exp\left(-b \cdot ADC_K + b^2 \cdot ADC_K^2 \cdot \frac{K}{6}\right)$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density $\rho$, wherein b is the diffusion encoding level, preferably determined for each pixel location, and wherein $ADC_K$ is a parameter for the apparent kurtosis diffusion coefficient, and wherein, K a parameter for the excess kurtosis, and wherein a non-linear least-squares method is used to obtain a fit.

Alternatively, in the case of diffusion-weighting, step d) above may be accomplished by processing said acquired or bias-corrected signal decays on a pixel by pixel basis to obtain the best possible fit between them and a non-mono-exponential equation of the form:

$$S(b) = S_0 \exp(-(bD)^\alpha)$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density ρ, wherein b is the diffusion encoding level, preferably determined for each pixel location, and wherein D is a parameter for a diffusion coefficient, and wherein a is a stretching parameter, and wherein a non-linear least-squares method is used to obtain a fit.

The method may further comprise the steps of:
i. furthermore performing k repeat measurements in step 1b; and
ii. arithmetically averaging k magnitude signal values obtained in i.
iii. wherein step 1f) uses an a that was determined according to the estimation of a mean value of absolute noise residuals as discussed above.

The method may further comprise the step of computing images with signal values between sampled values and outside the acquired range.

According to another aspect of the invention, there is provided an apparatus for highly reliable inference of signal and bias in weighted images, the weighted images being at least one of diffusion weighted, echo time weighted and repetition time weighted images, said apparatus comprising a controller arranged to:
a) receiving a set of magnitude signal decays from a patient obtained by a magnetic resonance imaging apparatus at each of a selected plurality of encoding levels distributed across a range of encoding levels within its capability, each said set of signal decays being representative of an image of a preselected cross-section of the patient, and each said signal decay of each said set corresponding to a pixel of its associated image;
b) setting the value of noise $\sigma_g$ for each pixel to 0 or a suitable very small value;
c) processing said acquired or bias-corrected signal decays on a pixel by pixel basis to obtain the best possible fit between them and a non-mono-exponential equation, wherein a non-linear least-squares method is used to obtain a fit;
d) determining $\theta_i = \hat{s}_i/\sigma_g$ for each fitted signal $\hat{s}_i$ as an estimate for the signal-to-noise ratio at each measured signal $s_i$;
e) obtaining for each pixel a first estimation of noise $\sigma_g$, taking into account the non-linear behavior of the noise distribution in relation to a true signal;
f) determining for each pixel the Rician signal bias $b_i$ for each fitted signal level $\hat{s}_i$ determined in d)
g) obtaining for each pixel a bias-corrected signal value $s_i^c$ by subtracting the Rician signal bias $b_i$ determined in g) from the measured signal level $s_i$ acquired in d);
h) repeating steps d) to h) until the change of $s_i^c$ falls under a predefined threshold.

The weighted images may be diffusion-weighted images, wherein the magnetic resonance imaging apparatus is capable of operation at different diffusion encoding levels, b-factors, at least between an upper and a lower limit, said lower limit preferably being below 500 sec/mm2, and more preferably below 300 sec/mm2, and most preferably below 150 sec/mm2, such as about 100 sec/mm2 or lower, and the upper limit preferably being above 2000 sec/mm2, and more preferably above 3000 sec/mm2, and most preferably about 5000 sec/mm2 or higher.

The weighted images may be echo-time weighted images, wherein the magnetic resonance imaging apparatus is capable of operation at different echo time encoding levels.

The weighted images may also be repetition time weighted images, wherein the magnetic resonance imaging apparatus is capable of operation at different repetition time encoding levels.

According to yet another aspect of the invention, there is provided a method for highly reliable non-mono-exponential fitting of diffusion-weighted images, said method comprising the steps of:
a) providing a magnetic resonance imaging apparatus capable of operation at diffusion encoding levels (b-factors) within a range ranging at least between an upper and a lower limit, said lower limit preferably being below 500 sec/mm2, and more preferably below 300 sec/mm2, and most preferably below 150 sec/mm2, such as about 100 sec/mm2 or lower, and the upper limit preferably being above 2000 sec/mm2, and more preferably above 3000 sec/mm2, and most preferably about 5000 sec/mm2 or higher;
b) acquiring a set of magnitude signal decays from a patient using said magnetic resonance imaging apparatus at each of a selected plurality of encoding levels distributed across the range of b-factors within its capability, each said set of signal decays being representative of an image of a preselected cross-section of the patient, and each said signal decay of each said set corresponding to a pixel of its associated image;
c) processing said acquired or bias-corrected signal decays on a pixel by pixel basis to obtain the best possible fit between them and a non-mono-exponential equation
d) wherein a non-linear least-squares method is used to obtain a fit.

In this method, the processing of said acquired or bias-corrected signal decays on a pixel by pixel basis in step c) can be made to obtain the best possible fit between them and a non-mono-exponential equation of the form:

$$S(b) = S_0 \exp\left(-b \cdot ADC_K + b^2 \cdot ADC_K^2 \cdot \frac{K_1}{6} - b^3 \cdot ADC_K^3 \cdot \frac{K_2^2}{27}\right)$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density ρ, wherein b is the diffusion encoding level, preferably determined for each pixel location, and wherein $ADC_K$ is a parameter for the apparent kurtosis diffusion coefficient, and wherein, $K_1$ is a parameter for the excess kurtosis, and wherein, $K_2$ is a second parameter for the excess kurtosis, and wherein $K_1$ and $K_2$ are expressed as predefined functions of $ADC_K$.

This method may also be combined with the method of the first aspect, wherein step c) is added at the end of the method of the first aspect.

The method may further comprise computing images with signal values between sampled values and outside the acquired range.

The results obtained may be displayed such that a zero value is displayed as a black pixel, and the larger the value the brighter the display of the associated pixel becomes.

According to yet another aspect of the invention, there is provided an apparatus for highly reliable non-mono-exponential fitting of diffusion-weighted images, said apparatus comprising a controller arranged to:
a) receive a set of magnitude signal decays from a patient obtained from a magnetic resonance imaging apparatus at each of a selected plurality of encoding levels distributed across a range of b-factors within its capability, each said set of signal decays being representative of an image of a preselected cross-section of the patient, and each said signal decay of each said set corresponding to a pixel of its associated image;
b) wherein said range of b-factors ranges at least between an upper and a lower limit, said lower limit preferably being below 500 sec/mm2, and more preferably below 300 sec/mm2, and most preferably below 150 sec/mm2, such as about 100 sec/mm2 or lower, and the upper limit preferably being above 2000 sec/mm2, and more preferably above 3000 sec/mm2, and most preferably about 5000 sec/mm2 or higher; and
c) processing said acquired or bias-corrected signal decays on a pixel by pixel basis to obtain the best possible fit between them and a non-mono-exponential equation, wherein a non-linear least-squares method is used to obtain a fit.

According to still another aspect of the invention, there is provided a method to infer numerically an estimation of a mean value of absolute noise residuals in a Rician signal distribution in magnitude signal data obtained with magnetic resonance imaging, said method comprising the steps of:
a) simulating a multitude of signal levels $\theta \geq 0$;
b) simulating for each signal level a multitude of realizations with the addition of Gaussian distributed random noise with $\sigma_g=1$;
c) forming the magnitude of each signal so realized in step b);
d) determining for each signal level $\theta$ the absolute value of the difference between original signal obtained in step a) and each value obtained in the previous step;
e) storing the arithmetic average of these differences obtained in step d) for each signal level $\theta$ as function values of $\alpha(\theta)$;
f) determining suitable linear interpolations for $\alpha(\theta)$.

In the method, after step c), a step forming arithmetic averages within groups of k such magnitude signals may be inserted.

According to still another aspect of the invention, there is provided an apparatus for inferring numerically an estimation of a mean value of absolute noise residuals in a Rician signal distribution in magnitude signal data obtained with magnetic resonance imaging, said apparatus comprising a controller arranged to:
a) simulating a multitude of signal levels $\theta \geq 0$;
b) simulating for each signal level a multitude of realizations with the addition of Gaussian distributed random noise with $\sigma_g=1$;
c) forming the magnitude of each signal so realized in step b);
d) determining for each signal level $\theta$ the absolute value of the difference between original signal obtained in step a) and each value obtained in the previous step;
e) storing the arithmetic average of these differences obtained in step d) for each signal level $\theta$ as function values of $\alpha(\theta)$;
f) determining suitable linear interpolations for $\alpha(\theta)$.

In accordance with the invention, an approach to estimate noise, Rician signal bias and true signal in magnitude signal data obtained with magnetic resonance imaging is provided. Rather than relying on repeat measurements for estimation of noise and expected signal at given scan parameter settings, the method uses multiple measurements at different scan parameter settings, also referred to as weightings, and an iterative algorithm to estimate noise, expected signal and associated Rician signal bias. The fact that the signal behavior in response to these weightings at individual image pixel locations can well be described with analytic functions is employed to infer and separate noise, expected signal and associated Rician signal bias at each weighting level measured. Measurements at all measured weighting levels contribute to the ultimate estimation of the bias-free signal decay function. Therefore, of the so processed magnetic resonance image data, weighted signals can be computed at arbitrary weighting levels and with considerably better signal-to-noise ratio than the originally obtained data at corresponding weightings. Bias-free weighted image data at desired weighting levels, maps of the decay function fit parameters, or maps of a combination of such decay function parameters can be used for rapid and highly sensitive tissue characterization.

Therefore, in the preferred embodiment of the method of the present invention, a magnetic resonance imaging apparatus is provided that is capable of performing diffusion-weighted magnetic resonance imaging using b-factors in the range between about 100 and 3000 sec/mm$^2$ and up to 5000 sec/mm$^2$ in the case of brain tissues. This apparatus is used to generate image data with signal-to-noise ratios at the lowest b-factor of 100:1 or below, across a selected anatomical slice at b-factors that are commonly equally spaced within the above stated range of b-factors, using at least one diffusion gradient encoding direction. For adequate stability of the non-mono-exponential fitting during image processing, the number of measurements should at least be twice as high as the number of free parameters of the non-mono-exponential fit. Moreover, it is assumed that the magnitude images produced by such magnetic resonance imaging apparatus exhibits signal values with Rician signal distributions. Accordingly, this condition would exclude images obtained with radio frequency coil-arrays and the so-called sum-of-squares reconstruction method.

Thus, the data acquired characterizes the diffusion-related signal decays in tissues according to a non-mono-exponential function on a pixel-by pixel basis. The method proceeds to determine the best fit of the measured decays to a non-mono-exponential function as discussed above with regard to the prior art. However, this determination is not made because it is believed that the best fit to the acquired data reflects the true signal decay. Instead it is made to establish an estimate of expected signal (S) and noise for each pixel at each b-factor measured.

The method makes use of the fact that the model functions, as discussed above with regard to the prior art, describe the signal decay well and that residual differences can be considered predominantly noise related. Since the non-mono-exponential fitting functions (except for the kurtosis function above the recommended upper bound $b \leq 3/(K \cdot ADC_K)$) are strictly monotonously decaying, there are no concerns that with increasing number of parameters the residuals vanish, as it is observed when data are over-fitted with polynomial expressions.

A first fit conducted over N samples provides fitted signals $\hat{s}_i$ that are estimates of the expected signals $\langle \hat{s}_i \rangle$. The absolute residuals between fitted signals $\hat{s}_i$ and measured signals $s_i$, i.e., $\hat{r}_i = |\hat{s}_i - s_i|$, respectively the squares of these residuals, are related to noise. For the squares of the residuals, a direct analytic solution for the adjustment of the non-linear relationship between the expected value of the square of the residual and noise can be found. For the absolute residuals, the consideration of the distribution of $r_i$ at each b-factor, leads to the conjecture that the mean or expected value of $\hat{r}_i$, i.e., $\langle \hat{r}_i \rangle = \alpha \cdot \sigma_g$, where $\sigma_g$ represents the noise of Gaussian distributed signals and where $\alpha$ is a function of signal-to-noise ratio. As the signal-to-noise ratio tends to infinity, Rician noise is similar to Gaussian noise and thus $\hat{r}_i$ follows a half-folded normal distribution with an expected value of $\sigma_g \cdot \sqrt{2/\pi}$. On the other hand, as the signal-to-noise ratio reaches zero, $\hat{r}_i$ follows a Rayleigh distribution with an expected value of $\sigma_g \cdot \sqrt{\pi/2}$. Thus, at these extremes, $\alpha$ reaches well known values.

The method relies on finding suitable values for $\alpha$ over the remaining range of signal-to-noise ratios. While an analytic function that describes $\alpha$ may exist, it is not necessary to know this function, since it can be determined numerically for a multitude of signal-to-noise ratios with satisfactory precision. Respective $\alpha$ values can be found through repeated Monte Carlo simulations of different complex signal values with known $\sigma_g$. After applying the magnitude operator to the complex signal, $\langle \hat{r}_i \rangle$ and consequently $\alpha$, using the relationship $\langle \hat{r}_i \rangle = \alpha \cdot \sigma_g$ introduced above, can be determined for different signal-to-noise ratios. With piecewise linear interpolation, it is possible to generate $\alpha$ values for the entire signal-to-noise range from 0 to $\infty$. The derivation of an approximated $\alpha$ function needs to only be performed once, since it does not depend on the functions to be fitted.

The next step is to obtain an initial estimate $\sigma_g$ for each pixel location. Again, assuming a perfect fit, an unbiased estimator of $\sigma_g$ at each b-factor can be obtained analytically as follows:

$$\frac{(\hat{s}_i - s_i)^2}{2\frac{\hat{s}_i}{\theta_i} + 2\theta_i \left( \hat{s}_i - \frac{\theta_i^2}{2\hat{s}_i^2} \left( \exp\left(-\frac{\theta_i^2}{4}\right) \sqrt{\frac{\pi}{2}} \frac{\hat{s}_i}{\theta_i} \left[ \left(\hat{s}_i^2 + 2\frac{\hat{s}_i^2}{\theta_i^2}\right) I_0\left(\frac{\theta_i^2}{4}\right) + \hat{s}_i^2 I_1\left(\frac{\theta_i^2}{4}\right) \right] \right) \right)}$$

where $\theta_i$ equals the SNR at $\hat{s}_i$. If we sum up all N estimations, we obtain a single unbiased estimator of $\sigma_g$ as follows:

$$\sigma_g = \frac{1}{N_f} \sum_1^N \frac{(\hat{s}_i - s_i)^2}{2\frac{\hat{s}_i}{\theta_i} + 2\theta_i \left( \hat{s}_i - \frac{\theta_i^2}{2\hat{s}_i^2} \left( \exp\left(-\frac{\theta_i^2}{4}\right) \sqrt{\frac{\pi}{2}} \frac{\hat{s}_i}{\theta_i} \left[ \left(\hat{s}_i^2 + 2\frac{\hat{s}_i^2}{\theta_i^2}\right) I_0\left(\frac{\theta_i^2}{4}\right) + \hat{s}_i^2 I_1\left(\frac{\theta_i^2}{4}\right) \right] \right) \right)}$$

where $N_f$ represents the degrees of freedom of the fit, which is a well-known concept in statistics. For most purposes, a sufficiently good approximate value for $N_f$ is $N - N_p$, where $N_p$ equals the number of free fit parameters, i.e., four in the case of a bi-exponential fit and three in the case of a gamma-distribution related fit, stretched exponential fit or kurtosis fit truncated to the second order polynomial. Moreover, where $\hat{s}_i$ is the best fit equation result and $s_i$ is the measured signal.

Alternatively, an initial estimate $\sigma_g$ for each pixel location can be performed with a numerical solution. Again, assuming a perfect fit, an unbiased estimator of $\sigma_g$ at each b-factor would be $\hat{r}_i / \alpha(\theta_i)$, where $\theta_i$, equals the SNR at $\hat{s}_i$. If we sum up all N estimations, we obtain a single unbiased estimator of $\sigma_g$ as follows:

$$\sigma_g = \frac{1}{N_f} \sum_1^N |\hat{s}_i - s_i| / \alpha(\theta_i)$$

where $N_f$ represents the degrees of freedom of the fit, which is a well-known concept in statistics. For most purposes, a sufficiently good approximate value for $N_f$ is $N - N_p$, where $N_p$ equals the number of free fit parameters, i.e., four in the case of a bi-exponential fit and three in the case of a gamma-distribution related fit, stretched exponential fit or kurtosis fit truncated to the second order polynomial. More accurate values for $N_f$ can be obtained through Monte Carlo simulations with respective fitting functions. Again, such Monte Carlo simulations only need to be performed once.

At this point in the process, the actual $\theta_i$ values are not known. But as an initial guess, a Gaussian signal distribution can be assumed for all $s_i$. After completing these calculation steps, initial guesses of $\sigma_g$ and of N expected signals $\langle s_i \rangle$ at respective b-factors have been obtained. For each $\hat{s}_i$ the Rician signal bias bi that would arise for the estimated $\sigma_g$ can then be calculated analytically according the following formula that is known in the field of signal processing:

$$b_i = \frac{1}{2\sigma_g^2} \left( \exp\left(-\frac{\hat{s}_i^2}{4\sigma_g^2}\right) \sqrt{\frac{\pi}{2}} \sigma_g \left[ (\hat{s}_i^2 + 2\sigma_g^2) I_0\left(\frac{\hat{s}_i^2}{4\sigma_g^2}\right) + \hat{s}_i^2 I_1\left(\frac{\hat{s}_i^2}{4\sigma_g^2}\right) \right] \right) - \hat{s}_i$$

Where $I_0$ and $I_1$ are zeroth and first order modified Bessel functions, respectively. The resulting bias value bi is then subtracted from the measured signal $s_i$ and finally a bias-corrected signal value $s_i^c$, to which again the model fit can be applied, is obtained. This process is performed iteratively to obtain increasingly better estimates of $\sigma_g$ and of N corrected signal values $s_i^c$ and their associated bias value $b_i$. At low signal-to-noise ratios, because of noise, the resulting corrected signal value $s_i^c$ may also be negative. The iteration process is terminated once the relative change of $s_i^c$ falls under a predefined level.

The same process can also be performed for previously averaged values, e.g., obtained through arithmetic averaging of k pixels over a region of interest assumed to present uniform diffusion. In this case, however, a different $\alpha$ function based on k averages has to be generated and used. If averaged diffusion signals were measured along different directions, however, this approach will not provide correct solutions, unless there is no or very low diffusion anisotropy. Instead, it is recommended to apply the method introduced above for each direction separately and then to geometrically average the corrected signal values $s_i^c$ that are obtained for the respective diffusion encoding directions.

Since the estimation of $\sigma_g$ in itself is prone to some variation, it may be considered beneficial to average $\sigma_g$ values that stem from analyses along different diffusion encoding directions. Indeed, $\sigma_g$ at a particular pixel location is expected to be the same, irrespective of diffusion encoding direction. Furthermore, in a typical setup with an array of radio-frequency coils, $\sigma_g$ is slowly varying and, therefore, $\sigma_g$ can be averaged over a larger number of pixels. Averaged $\sigma$—values so obtained, can then be applied in a final bias correction without further iteration. A final fitting is then applied to the so obtained corrected signal values $s_i^c$ and arbitrary diffusion-weightings, even outside the original b-factor range, can be generated for maximum lesion conspicuity. This final fitting does not necessarily need to rely on the same model function that was used to infer $\sigma_g$ before averaging.

Indeed it may be beneficial to apply a kurtosis fit with a truncated Taylor expansion, since the parameter $ADC_K$ is compatible with the conventional ADC. There are other benefits, which only become evident once the relationship between $ADC_K$ and K observed in certain tissues is investigated. As can be shown with diffusion measurements in tissues of normal prostate and prostate cancer, $ADC_K$ and K values that result from the application of the kurtosis model are highly correlated. A virtually identical correlation can be observed in brain white matter. Meanwhile, brain gray matter does not exhibit such correlation. While the absence of such correlation may be explained by the particular microarchitecture of brain gray matter, there is good reason to believe that such correlation can be observed in many other tissues, including different types of tumor.

Assuming that such correlation $ADC_K$ and K has been confirmed for the tissue of interest, it is possible to replace the K parameter in the kurtosis model fit function with a known function, with $ADC_K$ as independent variable. Several benefits materialize once this approach is employed:
  i. The reduction of unknown parameters by one results in improved fitting stability and, thus, less noisy estimates of $ADC_K$ and expected signals $\langle \hat{s}_i \rangle$.
  ii. For optimal lesion conspicuity, diffusion image data obtained at conventional b-factors below 1000 sec/mm² can be extrapolated to higher b-factors.
  iii. Measurements that include b-factors slightly above 1000 sec/mm², but where the range of b-factors is insufficient to support non-mono-exponential analysis, can be analyzed correctly. This implies, that diffusion imaging protocols, which use different b-factors slightly above 1000 sec/mm², yield fully comparable $ADC_K$ values.
  iv. System-specific non-linearities of the magnetic field gradients, which result in spatially variable b-factors can be fully corrected, even if the range of b-factors is insufficient to support non-mono-exponential analysis.
  v. Quantification of the perfusion-related diffusion component below 300 sec/mm² becomes more reliable, since any minor deviations from a basic mono-exponential model, even at b-factors below 1000 sec/mm², are fully accounted for.
  vi. The model yields non-mono-exponential signal decays even if only two b-factors were measured, e.g., b=100 and 1000 sec/mm².

For improved fits, particularly for fits beyond the recommended upper bound b≤3/(K·$ADC_K$), the Taylor expansion of the decaying exponential in the kurtosis model function can be extended by additional higher order terms. The resulting Taylor expansion truncated to the third order polynomial in b equals:

$$S(b) = S_0 \exp\left(-b \cdot ADC_K + b^2 \cdot ADC_K^2 \cdot \frac{K_1}{6} - b^3 \cdot ADC_K^3 \cdot \frac{K_2^2}{27}\right)$$

Where $K_1$ and $K_2$ represent tissue specific excess kurtosis coefficients. For diffusion coefficients that are distributed according to a gamma function it can be shown that $K_1=K_2$. In tissues, a situation with strictly gamma distributed diffusion coefficients does not necessarily apply, but as can be shown with diffusion measurements in brain over an extended b-factor range up to 5000 sec/mm², $K_1$ and $K_2$ show a relationship that is close to linear. This implies that at least for brain tissue this relationship can be exploited to obtain improved fits for measurements that exceed the recommended upper bound b≤3/(K·$ADC_K$) and that this relationship may be combined with the relationship between $ADC_K$ and K.

The present invention essentially establishes for each pixel position an estimation of the noise prevalent in the data. This is achieved with non-mono-exponential fit functions that describe the tissue signal adequately well, so that noise can be considered the primary source of the observed difference between fit and measured signal. In this new approach, it is furthermore taken into account that the residuals, which for each level of signal are proportional to the noise, vary in a non-linear fashion with the signal. This non-linear behavior, even if signals have been averaged with repeat measurements, can be established with simulations. The relationship so determined can be applied iteratively for the correct integration of all residuals at each signal level measured to obtain an accurate estimate of noise, which then, furthermore can be directionally and spatially averaged. Subsequently, the noise estimate can be applied to estimate Rician signal bias at each level along the signal decay curve and accordingly signals at each b-factor measured can be corrected. After completing the inference of noise and bias any suitable non-mono-exponential function can be applied to the corrected signal data. A new approach for such a function, which is presented here, exploits observations made that fit parameters measured in tissues correlate, when determined with kurtosis model functions based on a truncated Taylor expansion. This permits the establishment of correlation functions for the parameters and consequently reduction of free parameters in the kurtosis fitting models. The reduced number of parameters, in turn, greatly stabilizes the determination of non-mono-exponential fits and fit parameters and also opens up the possibility to apply non-mono-exponential fits for signal decays measured over a limited range and number of b-factors.

These novel approaches presented herein allow the present invention to provide well defined, free of signal bias, non-invasive imaging of tumor pathology and the clear differentiation of such pathology from surrounding normal tissue. Moreover, parameter maps can be generated that consistently only reflect underlying tissue parameters, that do not depend on protocol parameter settings and that are free of effects from non-linearities of the magnetic field gradients. Such parameter maps will permit better differentiation among pathologies, better comparison among different sites, and, furthermore, better establishment of universal cut-off values for tissue classification. Moreover, signal-to-noise ratio maps, which readily can be derived from the measured signal $s_i$ at the lowest b-factor and $\sigma_g$, can be considered very useful for protocol planning.

BRIEF DESCRIPTION OF THE DRAWINGS

These and other objects and advantages of the present invention will be better understood by those skilled in the art in view of the following detailed description of a preferred embodiment of the invention rendered in conjunction with the appended drawings. In appended drawings, like reference numerals are utilized to refer to like elements throughout, and.

DETAILED DESCRIPTION OF PREFERRED EMBODIMENTS

Figure 1:
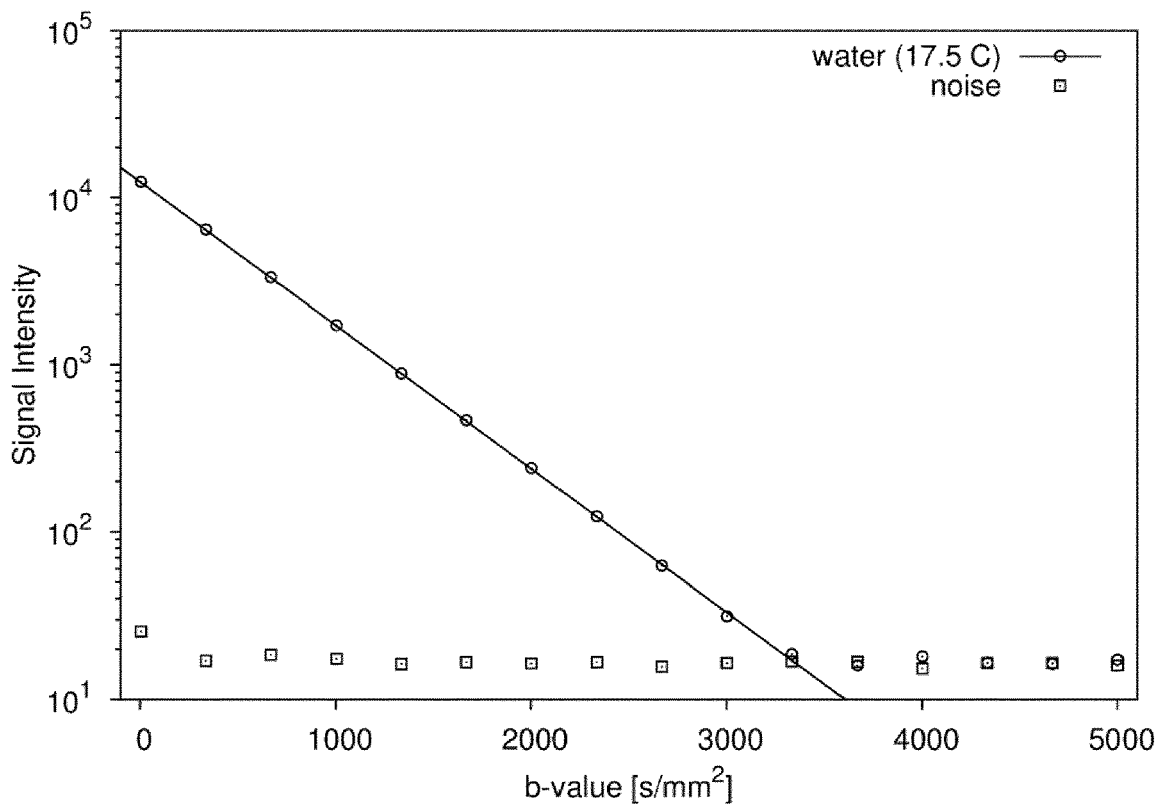
FIG. 1 is an illustrative graphical representation of the logarithmic decay signal intensity from pure water at 17.5 C as a function of b-factor.
Figure 2:
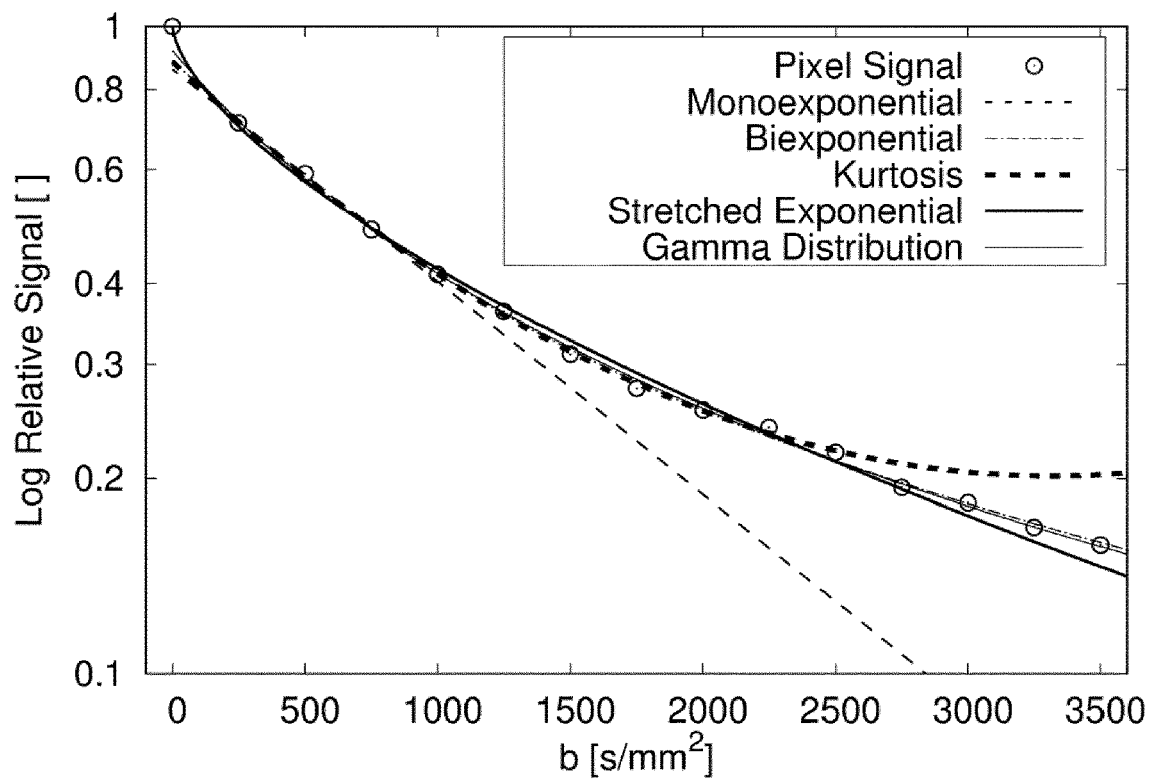
FIG. 2 is an illustrative graphical representation of the logarithmic decay signal intensity in tissue as a function of b-factor, with mono-exponential and non-mono-exponential model fits.
Figure 3:
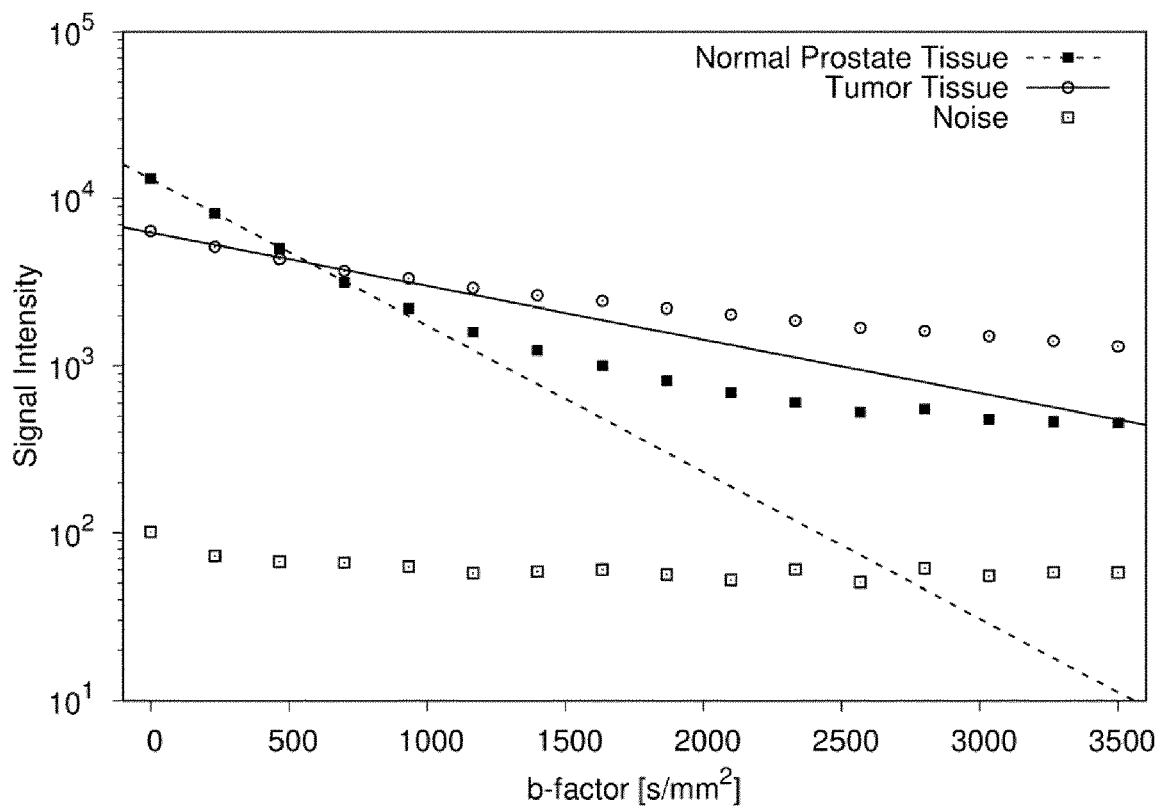
FIG. 3 is an illustrative graphical representation of the logarithmic decay signal intensity in normal prostate and prostate tumor tissue as a function of b-factor, with respective mono-exponential fits for b-factors up to 1000 sec/mm².
Figure 4A:
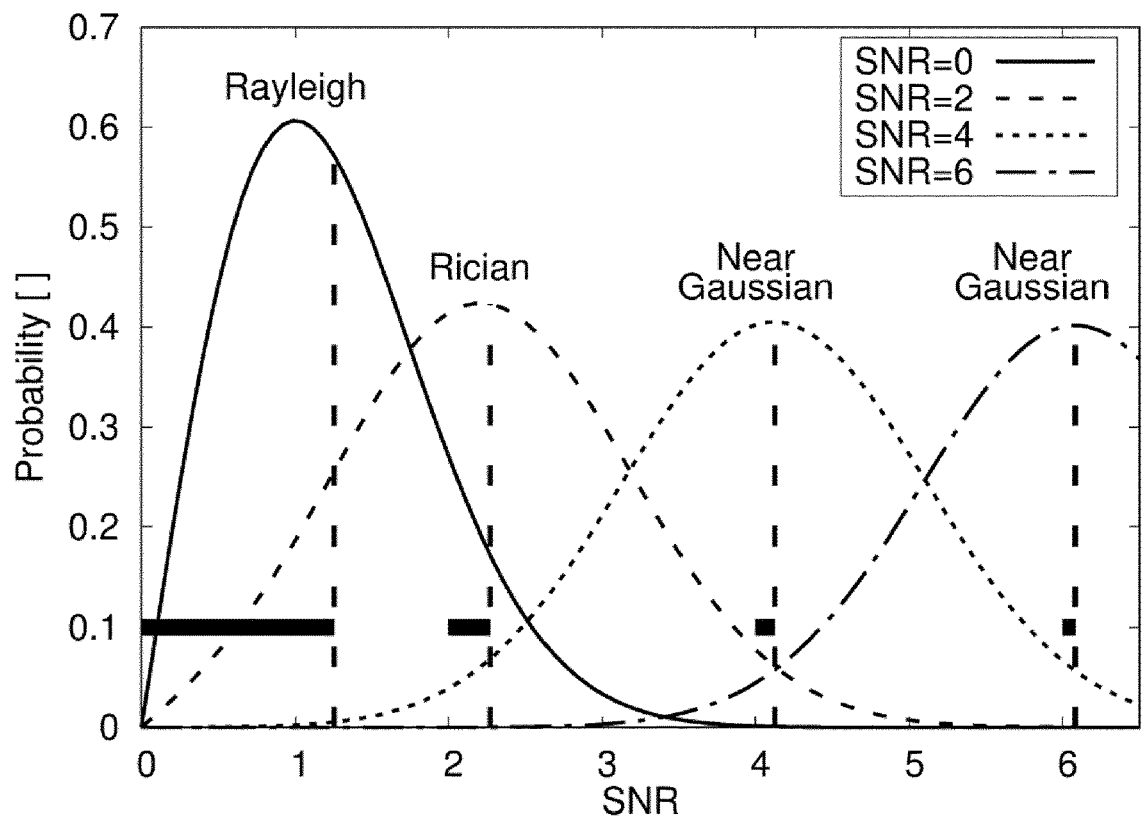
FIGS. 4A and 4B are illustrative graphical representations of Rician signal probability density distributions and their expectation values (FIG. 4A), as well as resulting bias (FIG. 4B) at low signal to noise ratios.
Figure 4B:
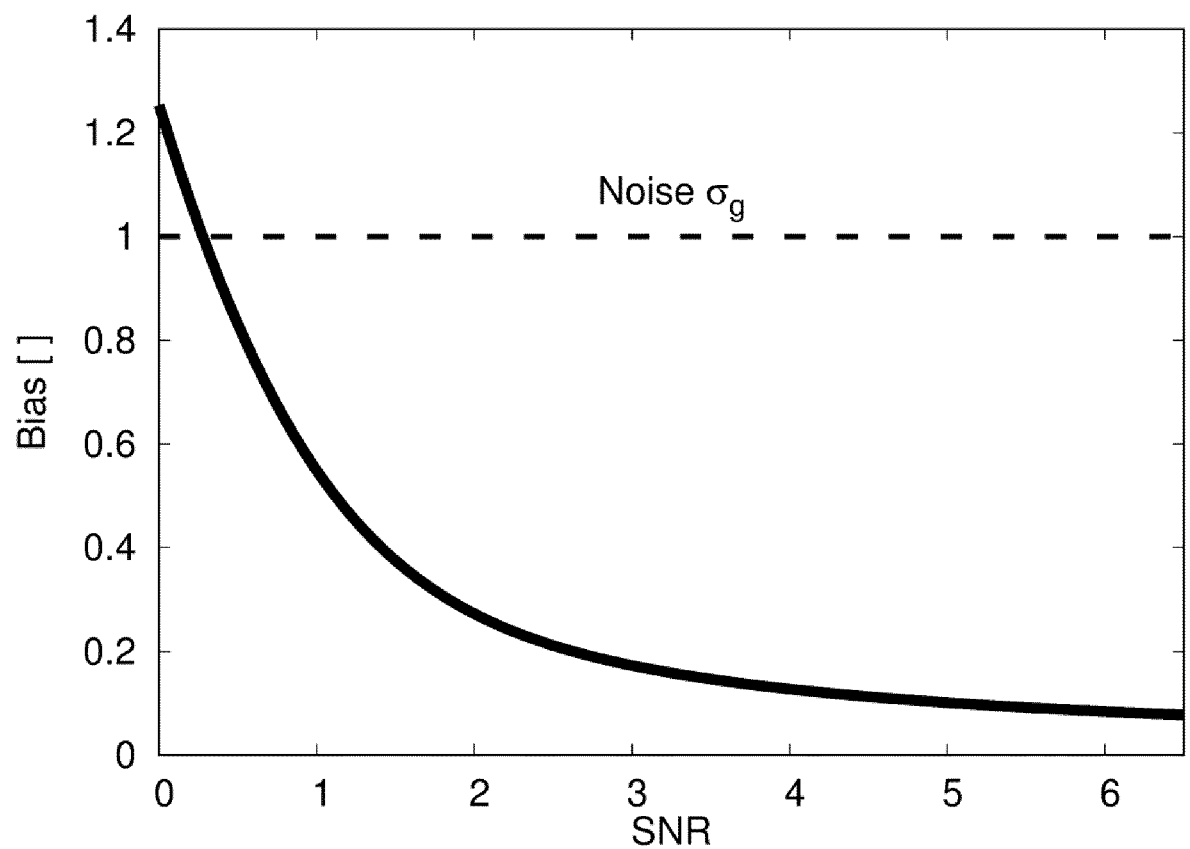
Figures 5A, 5B:
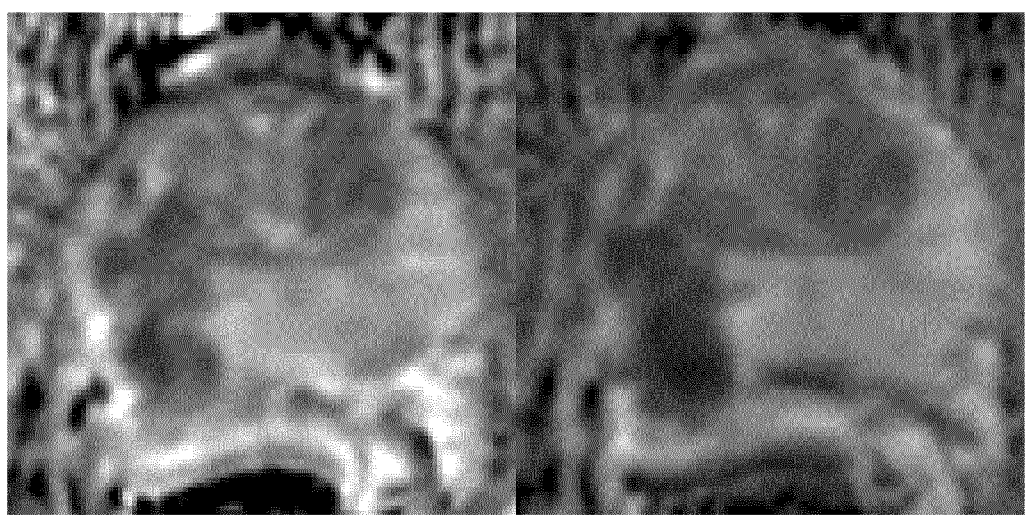
FIGS. 5A and 5B are illustrative graphical representations of ADC maps of prostate cancer obtained with maximum b-factors of 500 sec/mm² (FIG. 5A) and 1400 sec/mm² (FIG. 5B)
Figure 6:
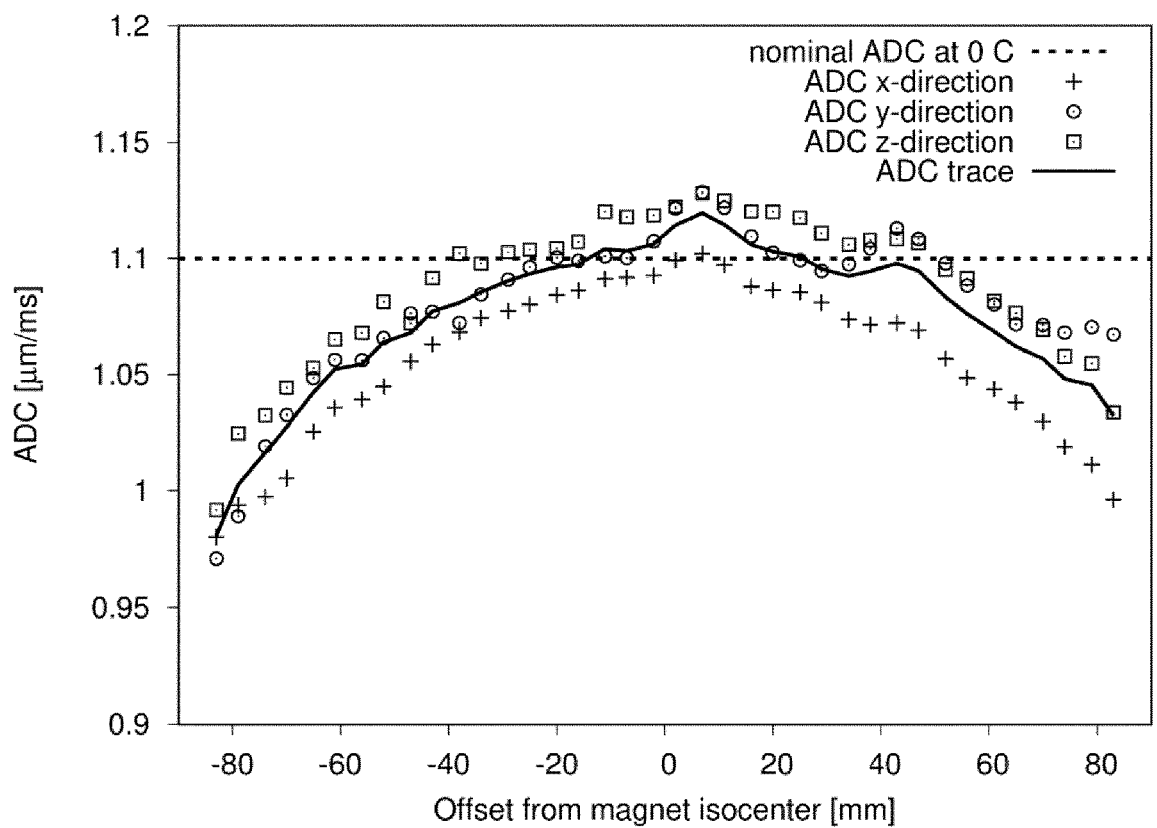
FIG. 6 is an illustrative graphical representation of the ADC measured with b-factors 0 and 1000 sec/mm² at different locations along the magnet principal axis in a water phantom surrounded with ice-water and a known ADC value of 1.1 μm²/ms at OC temperature.

As alluded to above, the present invention arises primarily from the observation that the tissue water diffusion signal strength vs. b-factor encoding level follows a non-mono-exponential function and that with signal-to-noise ratios prevalent on clinical imaging systems, this signal decay along an arbitrary diffusion encoding direction, but with b-factors higher than 100 to 300 sec/mm², can adequately be described with basic non-mono-exponential model functions that use four parameters or less. Specifically, diffusion experiments in tissues at different signal to noise ratios suggest that model-related differences are exceedingly small and, therefore, for typical signal-to-noise any differences between model fit and measured signals are primarily noise related.

If this observation is true, there is significant potential for the use of such model functions to infer noise in diffusion-weighted magnetic resonance imaging experiments. This in turn, permits the determination and elimination of signal bias that is introduced by the conversion of the complex magnetic resonance signal to a magnitude signal. The method, furthermore, very efficiently can obtain bias-free diffusion-weighted images with excellent signal-to-noise ratio for arbitrary diffusion weighting levels for optimal viewing of lesions, whereas conventional acquisition protocols rely on signal averaging at selected b-factors to obtain bias-contaminated diffusion-weighted images with acceptable signal-to-noise ratio. Moreover, the method provides accurate so-called "apparent diffusion coefficients" that can be largely independent of imaging protocol design and magnetic field gradient non-linearities. The ramifications of this are significant as will be discussed in greater detail in the example below.

The various steps of the method of the invention now will be discussed. These steps include:

(1) simulating a multitude of signal levels θ and simulating for each signal level a multitude of realizations with the addition of Gaussian distributed random noise with $\sigma_g=1$. Determining for each signal level and each realization the absolute difference between original signal θ and the magnitude of the signals with noise added. Storing the arithmetic average of these differences for each signal level θ as function values of $\alpha(\theta)$;

(2) alternatively, simulating a multitude of signal levels θ and simulating for each signal level a multitude of realizations with the addition of Gaussian distributed random noise with $\sigma_g=1$. Forming the magnitude of each signal so realized and generating arithmetic averages within groups of k such magnitude signals. Determining for each signal level θ the absolute difference between original signal and each averaged magnitude signal with incorporated noise. Storing the arithmetic average of these differences for each signal level θ as function values of $\alpha(\theta)$;

(3) determining suitable linear interpolations for $\alpha(\theta)$;

(4) the provision of an appropriate magnetic resonance imaging apparatus;

(5) acquiring a plurality of sets of signals from a patient using the magnetic resonance imaging apparatus at each of a selected number of encoding levels distributed across a wide range of b-factors along at least one diffusion encoding direction;

(6) setting or initializing the value of the noise $\sigma_g$ for each pixel to 0 or a suitable very small value;

(7) processing the acquired or bias-corrected signal decays on a pixel by pixel basis to obtain the best possible fit between them and a non-mono-exponential equation of the form:

$$S(b)=S_0(f \cdot \exp(-bD_f)+(1-f) \cdot \exp(-bD_s))$$

In this equation, $S_0$ is a constant that depends on constant values associated with (a) the magnetic imaging apparatus, (b) the spin-spin relaxation time T2, (c) the spin lattice relaxation time T1, and (d) the spin density ρ. Also, b is the diffusion encoding level, preferably determined for each pixel location, $D_f$ and $D_s$ describe the diffusion coefficients of two compartments with fast and slow diffusion, respectively, and the fraction $f$ is used to account for the relative signal contribution of each compartment. Preferably, the best fit is obtained with an advanced non-linear least-square method such as the Levenberg-Marquardt algorithm;

(8) alternatively, processing the acquired or bias-corrected signal decays on a pixel by pixel basis to obtain the best possible fit between them and a non-mono-exponential equation of the form:

$$S(b) = \frac{S_0}{(1+\theta b)^k}$$

In this equation, $S_0$ is a constant that depends on constant values associated with (a) the magnetic imaging apparatus, (b) the spin-spin relaxation time T2, (c) the spin lattice relaxation time T1, and (d) the spin density ρ. Also, b is the diffusion encoding level, preferably determined for each pixel location, and k and θ are a shape and scaling parameter, respectively, of a gamma distribution that is associated with this function. Preferably, the best fit is obtained with an advanced non-linear least-square method such as the Levenberg-Marquardt algorithm;

(9) alternatively, processing the acquired or bias-corrected signal decays on a pixel by pixel basis to obtain the best possible fit between them and a non-mono-exponential equation of the form:

$$S(b) = S_0 \exp\left(-b \cdot ADC_K + b^2 \cdot ADC_K^2 \cdot \frac{K}{6}\right)$$

In this equation, $S_0$ is a constant that depends on constant values associated with (a) the magnetic imaging apparatus, (b) the spin-spin relaxation time T2, (c) the spin lattice relaxation time T1, and (d) the spin density ρ. Also, b is the diffusion encoding level, preferably determined for each pixel location, K a parameter termed excess kurtosis and $ADC_K$ the apparent kurtosis diffusion coefficient. Preferably, the best fit is obtained with an advanced non-linear least-square method such as the Levenberg-Marquardt algorithm;

(10) alternatively, processing the acquired or bias-corrected signal decays on a pixel by pixel basis to obtain the best possible fit between them and a non-mono-exponential equation of the form:

$$S(b)=S_0 \exp(-(bD)^\alpha)$$

In this equation, $S_0$ is a constant that depends on constant values associated with (a) the magnetic imaging apparatus, (b) the spin-spin relaxation time T2, (c) the spin lattice relaxation time T1, and (d) the spin density ρ. Also, b is the diffusion encoding level, preferably determined for each pixel location, and D and a parameters that determine the shape of the decay curve. This model is recommended to account for perfusion effects and, therefore, a measurement at a very low or zero b-factor should be included. Preferably, the best fit is obtained with an advanced non-linear least-square method such as the Levenberg-Marquardt algorithm;

(11) determining $\theta_i=\hat{s}_i/\sigma_g$ for each fitted signal $\hat{s}_i$ as an estimate for the signal-to-noise ratio at each measured signal $s_i$;

(12) obtaining for each pixel a first estimation of noise $\sigma_g$ by performing the following computation:

$$\sigma_g = \frac{1}{N_f} \sum_1^N \frac{(\hat{s}_i - s_i)^2}{2\frac{\hat{s}_i}{\theta_i} + 2\theta_i\left(\hat{s}_i - \frac{\theta_i^2}{2\hat{s}_i^2}\left(\exp\left(-\frac{\theta_i^2}{4}\right)\sqrt{\frac{\pi}{2}}\frac{\hat{s}_i}{\theta_i}\left[\left(\hat{s}_i^2 + 2\frac{\hat{s}_i^2}{\theta_i^2}\right)I_0\left(\frac{\theta_i^2}{4}\right) + \hat{s}_i^2 I_1\left(\frac{\theta_i^2}{4}\right)\right]\right)\right)}$$

where N equals the number of b-factors to be analyzed, $N_f=N-N_p$, and $N_p$ equals the number of free fit parameters. Moreover, wherein α was determined according to step (1) or, if averaging is performed, according to step (2), and $\hat{s}_i$ is the best fit equation result and $s_i$ is the measured signal;

(13) alternatively, obtaining for each pixel a first estimation of noise $\sigma_g$ by performing the following computation:

$$\sigma_g = \frac{1}{N_f} \sum_{1}^{N} |\hat{s}_i - s_i| / \alpha(\theta_i)$$

where N equals the number of b-factors to be analyzed, $N_f = N - N_p$, and $N_p$ equals the number of free fit parameters. Moreover, wherein α was determined according to step (1) or, if averaging is performed, according to step (2), and $\hat{s}_i$ is the best fit equation result and $s_i$ is the measured signal;

(14) determining for each pixel the Rician signal bias $b_i$ for each fitted signal level $\hat{s}_i$ according to the equation (see, Koay C G and Basser P J.; Analytically Exact Correction Scheme for Signal Extraction from Noisy Magnitude MR Signals, *Journal of Magn Reson*, 179: 317-322, 2006):

$$b_i = \frac{1}{2\sigma_g^2}\left(\exp\left(-\frac{\hat{s}_i^2}{4\sigma_g^2}\right)\sqrt{\frac{\pi}{2}}\sigma_g\left[(\hat{s}_i^2 + 2\sigma_g^2)I_0\left(\frac{\hat{s}_i^2}{4\sigma_g^2}\right) + \hat{s}_i^2 I_1\left(\frac{\hat{s}_i^2}{4\sigma_g^2}\right)\right]\right) - \hat{s}_i$$

(15) obtaining for each pixel a bias-corrected signal value $s_i^c$ by subtracting the Rician signal bias $b_i$ from the measured signal level $s_i$;
(16) repeating steps (7) to (15), but without changing the fitting function, until the change of $s_i^c$ falls under a predefined threshold;
(17) averaging arithmetically on a pixel by pixel basis the $\sigma_g$ values determined along different diffusion encoding directions;
(18) performing a spatial averaging of the directionally averaged $\sigma_g$ values;
(19) dividing on a pixel by pixel basis $s_i$ measured at the lowest b-factor with $\sigma_g$ as processed in steps (17) and (18) and to store the resulting values as signal-to-noise ratio map;
(20) repeating steps (14) and (15) with $\sigma_g$ as processed in steps (17) and (18) to obtain for each pixel a final set of bias-corrected signal values $s_i^c$;
(21) processing bias-corrected signal decays on a pixel by pixel basis to obtain the best possible final fit with any non-mono-exponential function, preferably one with low number of free parameters such as an equation of the form:

$$S(b) = S_0 \exp\left(-b \cdot ADC_K + b^2 \cdot ADC_K^2 \cdot \frac{K_1}{6} - b^3 \cdot ADC_K^3 \cdot \frac{K_2^2}{27}\right)$$

In this equation, $S_0$ is a constant that depends on constant values associated with (a) the magnetic imaging apparatus, (b) the spin-spin relaxation time T2, (c) the spin lattice relaxation time T1, and (d) the spin density ρ. Also, b is the diffusion encoding level, preferably determined for each pixel location, $ADC_K$ the apparent kurtosis diffusion coefficient, and $K_1$ and $K_2$ excess kurtosis parameters that are expressed as functions of $ADC_K$. Preferably, the best fit is obtained with an advanced non-linear least-square method such as the Levenberg-Marquardt algorithm;
(22) displaying arithmetic averages of resulting direction-dependent parameter maps and geometric averages of the direction-dependent fitted signals for each b-factor sampled, or any other b-factor level inside or outside the sampled range of b-factors.

Some of the data presented herein was obtained with line scan diffusion imaging. This technique and an apparatus suitable for practice thereof is described in detail in U.S. Pat. No. 5,786,692 issued on Jul. 28, 1998 to Stephan E. Maier, et al. and entitled "Line Scan Diffusion Imaging", which is hereby incorporated by reference into this specification. The suitability of this technique for diffusion imaging at high b-factors is documented in detail in U.S. Pat. No. 6,751,495 issued on Jun. 15, 2004 to Stephan E. Maier et al. and entitled "Method of Fast and Reliable Tissue Differentiation Using Diffusion-Weighted Magnetic Resonance Imaging", which is hereby incorporated by reference into this specification.

The preferred embodiment of the invention herein described illustratively adopts the single-shot echo planar imaging technique (see, Turner R, Le Bihan D, Maier J, Vavrek R, Hedges L K, and Pekar J.; Echo-Planar Imaging of Intravoxel Incoherent Motions, *Radiology*, 177:407-414, 1990). This imaging method appears to be suitable for rapidly obtaining largely motion artifact free images even at very high b-factors of up to 5000 sec/mm². An apparatus and pulse sequence suitable for the practice thereof, as will be seen from FIGS. 7 and 8, includes a magnetic resonance imaging system 10, generally having a magnet assembly, interface circuitry, and a computer 40. The magnet assembly includes a very strong magnet 13 that creates a homogeneous magnetic field within and around a sample (e.g. an inert sample or patient). X, Y, and Z magnetic field gradient coils 14, 16, and 18 also form a part of the assembly and are positioned proximate or surrounding the sample 20. The assembly further comprises one or more RF coils 22, which are positioned near or around the sample.

The interface circuitry includes a gradient waveform generator 24 that has signal outputs connected to the gradient coils 14, 16, and 18, and a control input connected to the computer and an output connected to an input of an RF power amplifier 28. The RF power amplifier has an output connected to an input of an RF switch 30. The RF power amplifier has an output connected to the RF coil 22, and has an output connected to the input of an RF detector 32.

The computer 40 includes computing hardware 42 and storage. The computing hardware can comprise special purpose hard-wired computing circuitry dedicated to magnetic resonance acquisition, an imaging and a special programmed general purpose computer, or a combination of both. The storage 46 can include various types of storage, such as disk storage and random access memory.

The storage can be used to store data and programs, including programs used to interact with the system's interface circuitry 12. The computer has a video output for providing video signals to a display 46, as well as control outputs connected respectively to control inputs of the gradient waveform generator 24 and the RF signal generator 26. The computer also has acquisition input operatively connected to an output of the RF detector 32.

Figure 7:
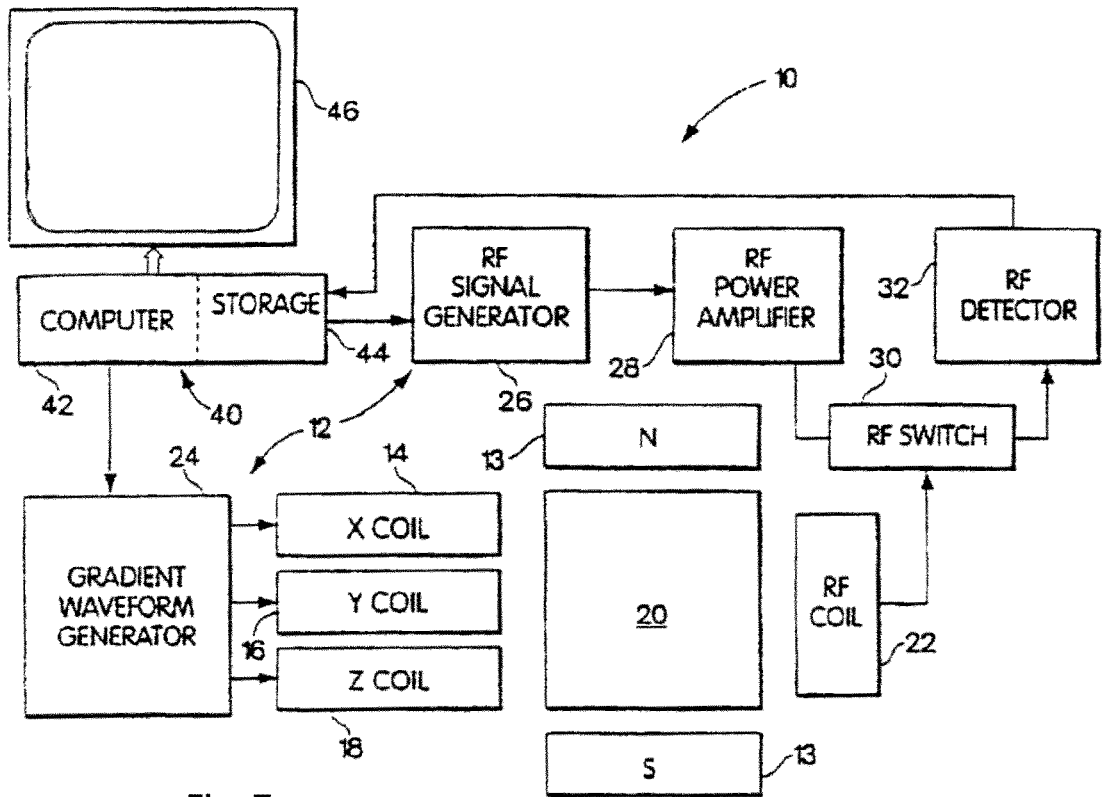
FIG. 7 is a high-level block diagram of an illustrative embodiment of a magnetic resonance imaging system suitable for use in the method of present invention.
Figure 8:
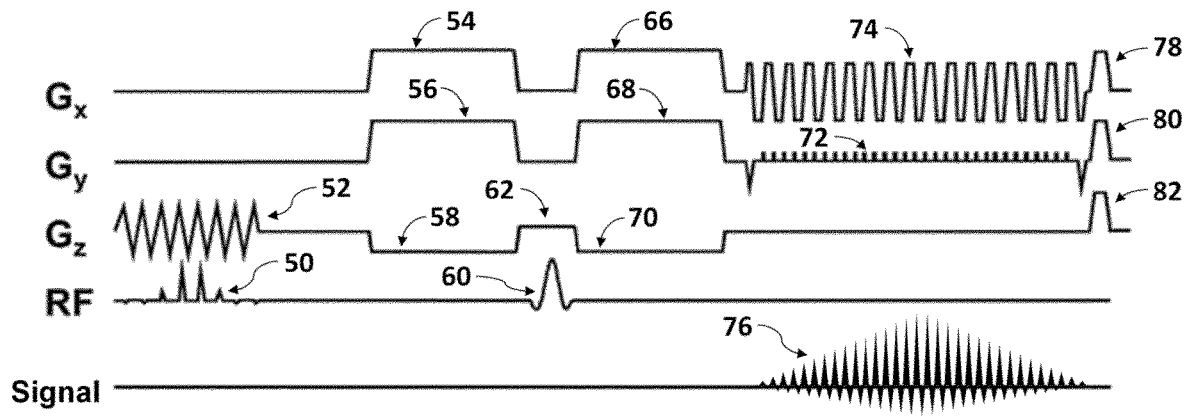
FIG. 8 is an imaging pulse sequence diagram for the acquisition of one image of data from a slice using the system illustratively depicted in FIG. 7.

In operation, referring to FIGS. 7 and 8, the imaging system 10 builds images sequentially under control of the computer 40 according to a single-shot echo-planar imaging (EPI) sequence. At the beginning of an acquisition sequence for an image, the computer 40 sends a signal to the RF signal generator 26, which responds by generating a water-selective 90⁰ pulse 50. This pulse is amplified by the RF power amplifier 28 and provided to the RF coil 22 via the RF switch 30. As this pulse is being provided, the computer instructs the gradient waveform generator 24 to drive the Z coil 16 with a slice and frequency-selective multi-polar pulse.

Next, the gradient waveform generator 24 provides a first set of diffusion gradient pulses 54, 56, and 58 respectively to the X, Y, and Z gradient coils 14, 16, and 18. These gradient signals each include a signal rectangular pulse, which is provided in order to sensitize the magnetic resonance imaging process to diffusion. After the falling edge of the diffusion gradient signals, a 180° pulse 60 is provided to the RF coil 22, in much the same way that the 90° pulse was. At the same time, the gradient waveform generator provides a rectangular pulse 62 on the Z gradient coil. This pulse is of shorter duration than the diffusion gradient pulses. Then, the waveform generator provides a second set of diffusion gradient signals 66, 68, and 70 respectively to the X, Y, and Z gradient coils 14, 16 and 18. These second diffusion gradient signals are of the same amplitude and duration as the first diffusion gradient signals. Once the second diffusion gradient signals are turned off, the gradient waveform generator provides repeated pulses 72 on the Y coil 16 for spatial encoding along the phase direction. At the same time, the gradient waveform generator provides repeated pulses 74 on the X coil 14 for spatial encoding along the frequency direction.

As a result of this excitation sequence, a train of echoes 76 is received from the slice that was excited by the 90° and 180° pulses. The RF coils receives these echoes and provides them via RF switch 30 to the RF detector. The computer 40 receives the output of the detector, and processes it to obtain one image to be displayed on the display 46. After the echo has been received, optional crusher gradient signals 78, 80, and 82 can be applied to the gradient coils 14, 16 and 18.

The method then proceeds with the acquisition of images from a patient using the magnetic resonance imaging apparatus at each of a selected plurality of encoding directions and of encoding levels distributed across the range of b-factors within its capability. This is accomplished by varying the gradient amplitude G along an arbitrary direction in the equation for the b-factor $b=\gamma^2 G^2 \delta^2(\Delta-\delta/3)$. Each of the acquired sets of signal decays is representative of an image of a selected anatomical cross-section of the patient. Further, each individual signal decay in each set corresponds to a pixel of its associated image.

In the preferred embodiment $\alpha(\theta)$ is determined without averaged signals. This involves a) simulating a multitude of signal levels $\theta$; b) simulating for each signal level a multitude of realizations with the addition of Gaussian distributed random noise with $\sigma_g=1$; c) determining for each signal level and each realization the absolute difference between original signal $\theta$ and the magnitude of the signals with noise added; d) storing the arithmetic average of these differences for each signal level $\theta$ as function values of $\alpha(\theta)$ and e) determining suitable linear interpolations for $\alpha(\theta)$. Next, data processing begins with a first setting of noise $\sigma_g$ for each pixel to 0 or a suitable very small value.

In the preferred embodiment the fitting model function is a bi-exponential decay function. The acquired or bias-corrected signal decays are processed on a pixel by pixel basis to obtain the best possible fit between them and a non-mono-exponential equation of the form:

$$S(b)=S_0(f \cdot \exp(-bD_f)+(1-f) \cdot \exp(-bD_s))$$

In this equation, $S_0$ is a constant that depends on constant values associated with (a) the magnetic imaging apparatus, (b) the spin-spin relaxation time T2, (c) the spin lattice relaxation time T1, and (d) the spin density $\rho$. Also, b is the diffusion encoding level, preferably determined for each pixel location, $D_f$ and $D_s$ describe the diffusion coefficients of two compartments with fast and slow diffusion, respectively, and the fraction $f$ is used to account for the relative signal contribution of each compartment. Preferably, the best fit is obtained with an advanced non-linear least-square method such as the Levenberg-Marquardt algorithm.

After completion of this step, $\theta_i = \hat{s}_i/\sigma_g$ is determined for each fitted signal $s_i$ as an estimate for the signal-to-noise ratio at each measured signal $s_i$. Then for each pixel a new estimate of noise $\sigma_g$ is obtained by performing the following computation:

$$\sigma_g = \frac{1}{N_f} \sum_1^N \frac{(\hat{s}_i - s_i)^2}{2\frac{\hat{s}_i}{\theta_i} + 2\theta_i\left(\hat{s}_i - \frac{\theta_i^2}{2\hat{s}_i^2}\left(\exp\left(-\frac{\theta_i^2}{4}\right)\sqrt{\frac{\pi}{2}}\frac{\hat{s}_i}{\theta_i}\left[\left(\hat{s}_i^2 + 2\frac{\hat{s}_i^2}{\theta_i^2}\right)I_0\left(\frac{\theta_i^2}{4}\right) + \hat{s}_i^2 I_1\left(\frac{\theta_i^2}{4}\right)\right]\right)\right)}$$

where N equals the number of b-factors to be analyzed, $N_f=N-N_p$, and $N_p$ equals the number of free fit parameters. Moreover, where $\hat{s}_i$ is the best fit equation result and $s_i$ is the measured signal.

Alternatively, for each pixel a new estimate of noise $\sigma_g$ is obtained by performing the following computation:

$$\sigma_g = \frac{1}{N_f}\sum_1^N |\hat{s}_i - s_i|/\alpha(\theta_i)$$

Where N equals the number of b-factors to be analyzed, $N_f=N-N_p$, and $N_p$ equals the number of free fit parameters. Moreover, where $\hat{s}_i$ is the best fit equation result and $s_i$ is the measured signal. Subsequently, for each pixel Rician signal bias $b_i$ is computed for each fitted signal level $s_i$ according the equation:

$$b_i = \frac{1}{2\sigma_g^2}\left(\exp\left(-\frac{\hat{s}_i^2}{4\sigma_g^2}\right)\sqrt{\frac{\pi}{2}}\sigma_g\left[(\hat{s}_i^2 + 2\sigma_g^2)I_0\left(\frac{\hat{s}_i^2}{4\sigma_g^2}\right) + \hat{s}_i^2 I_1\left(\frac{\hat{s}_i^2}{4\sigma_g^2}\right)\right]\right) - \hat{s}_i$$

Finally, for each pixel a bias-corrected signal value $s_i^c$ is obtained by subtracting the Rician signal bias $b_i$ from the measured signal level $s_i$. Fitting, signal-to-noise ratio calculation, noise estimation, bias calculation, and bias subtraction from the measured signal are repeated until the change of $s_i^c$ falls under a predefined threshold.

In the preferred embodiment, $\sigma_g$ measured along the different diffusion encoding directions is arithmetically averaged and the resulting maps are low pass filtered. The $\sigma_g$ so obtained is used to perform a final bias calculation and bias subtraction from the measured signal. The bias-corrected signal value $s_i^c$ is then again fitted with a non-mono-exponential function that uses as few parameters as possible. With the resulting fit parameters and the fit function, images of b-factors outside acquired range are computed. For each pixel, the signal value $s_i$ measured at the lowest b-factor is divided with the pixel specific $\sigma_g$ and the resulting data is stored as signal-to-noise ratio map. As last step, arithmetic averages of resulting direction-dependent parameter maps and geometric averages of the direction-dependent fitted signals for each b-factor sampled, or any other b-factor level inside or outside the sampled range of b-factors are displayed on the computer monitor 46.

The following example will further describe the invention in terms of the actual experimental process, which led to its creation.

Example

With wide b-factor range diffusion scans it has been demonstrated that in prostate and human brain water signal attenuation is better described with non-mono-exponential models than a mono-exponential model as it is generally used in clinical applications. The data presented herein is the result of processing diffusion-weighted image data obtained in patients and normal subjects. Diffusion-weighted images of the prostate were obtained with the single-shot echo planar imaging technique on two different 3 Tesla magnetic resonance imaging systems. Diffusion-weighted images of the brain were obtained with line scan diffusion imaging on a 1.5 Tesla magnetic resonance imaging system.

For the prostate scans in patients, one setup included a 3 Tesla Philips Achieva (Philips, Eindhoven, NL) scanner with the capability to deliver 40 mT/m maximum gradient strength along each axis. Conventional diagnostic imaging with an external RF coil array and two-fold parallel coil acceleration included a diffusion scan of 4 min duration, where images at b-factors 0, 500, 1000 and 1500 sec/mm$^2$ at isotropic spatial resolution of 3×3×3 mm$^3$ were obtained. For each of these b-factors, measurements were performed along three orthogonal diffusion encoding directions. Moreover, each measurement was repeated six times and resulting magnitude signals were averaged. The same spatial resolution and coil setup with two-fold acceleration was employed for a wide range b-factor scan that was performed to obtain data for the proposed processing. For this scan of 3 min duration, 21 evenly spaced b-factor measurements between 0 and 3000 sec/mm$^2$ were performed along three orthogonal diffusion encoding directions.

A second setup employed for prostate scans in patients, included a 3 Tesla GE Discovery MR750 (General Electric Medical Systems, Milwaukee, Wis.) system with the same gradient capability, but with a single-channel endo-rectal coil (Medrad, Pittsburgh, Pa.). In a 3 min scan, diffusion-weighted images were obtained with an in-plane resolution of 4.4×4.4 mm$^2$ and 5 mm slice thickness for 15 evenly spaced b-factors between 0 and 3500 sec/mm$^2$ and three orthogonal diffusion encoding directions.

Scans in brains of normal volunteers were performed on a 1.5 Tesla Horizon Echospeed (GE Medical Systems, Milwaukee, Wis.) system with 22 mT/m maximum gradient strength along each axis. Line scan diffusion images with an in-plane resolution of 3.4×3.4 mm$^2$ and 6 mm slice thickness were obtained with a conventional quadrature head coil without parallel acceleration. Diffusion encoding was performed for 32 evenly spaced b-factors between 5 and 5000 sec/mm$^2$ and along 6 non-collinear and non-coplanar directions. The scan time for a single mid-ventricular axial slice was 27 min.

Figure 9A:
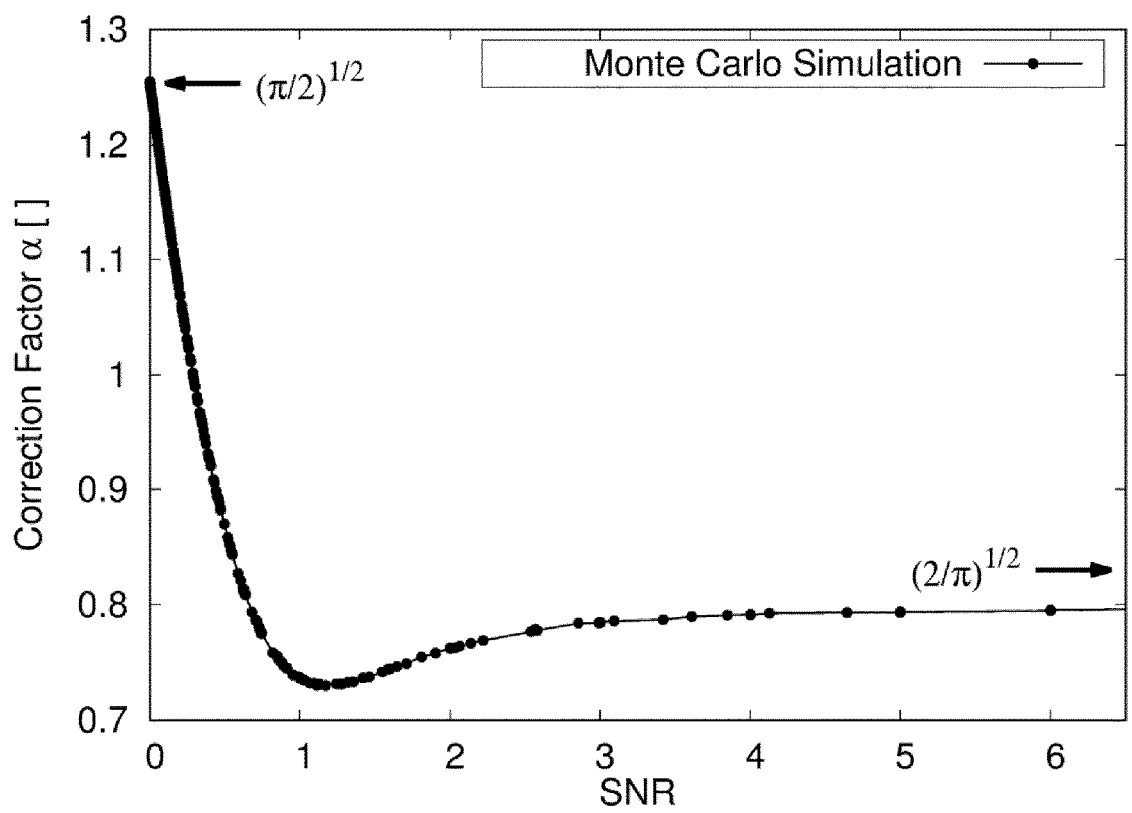
FIGS. 9A and 9B are illustrative graphical representations of the correction function a without averaging (FIG. 9A) and with averaging (FIG. 9B) determined with Monte Carlo simulations for signal-to-noise ratios between 0 and 6.
Figure 9B:
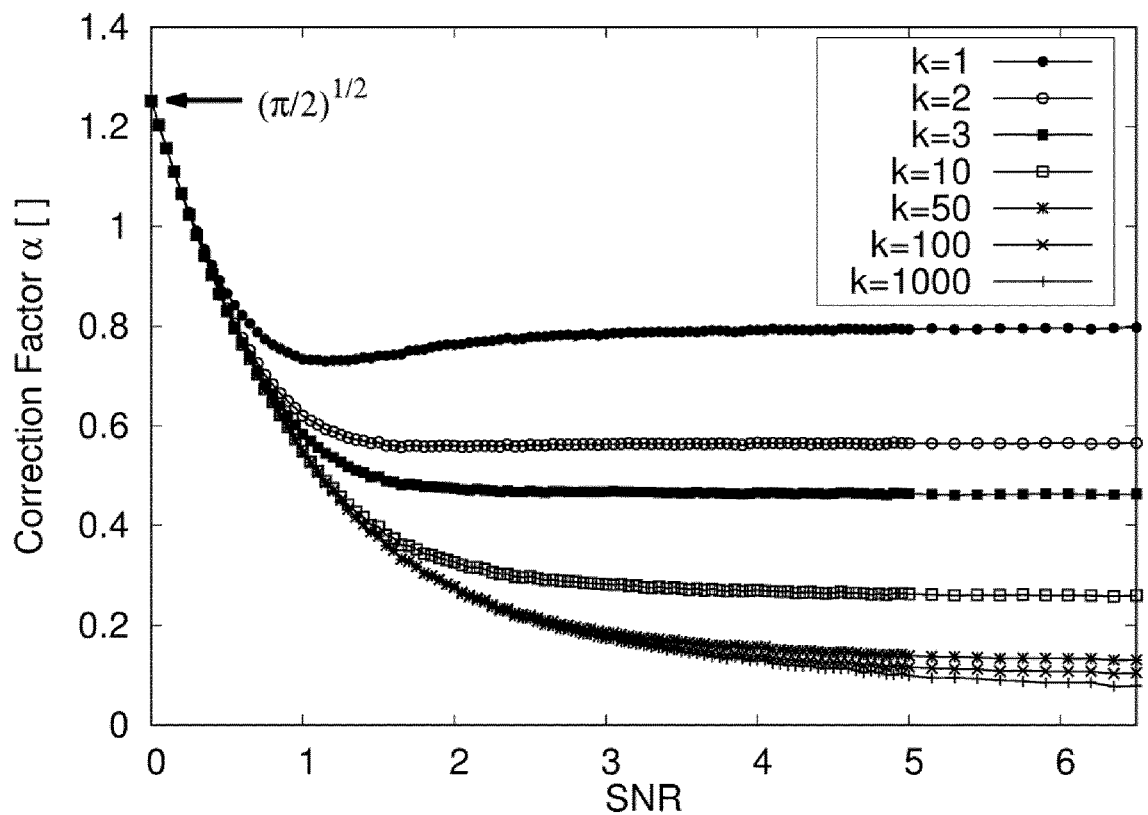

As outlined in the summary of the invention, in a preparatory processing step, a as a function of signal-to-noise ratio has to be determined. FIG. 9A shows the function so obtained without averaging for a signal-to-noise ratio between 0 and 6. FIG. 9B shows the same curve (k=1), but also curves for different number of averages k.

The processing algorithm was implemented on a personal computer with an Intel 4-core i7-6700 CPU 3.40 GHz chip and a Gentoo Linux operating system with 4.14.65 kernel. The final version was implemented with Python version 3.6.5 software. Non-linear least-square fitting was performed with the predefined algorithm "scipy.optimize.curve_fit", version 0.19.1. For each non-mono-exponential function, suitable parameter start values and value bounds were defined. Typical processing time with this setup was around 30 min per slice and typical number of iterations required equaled three.

Figure 10:
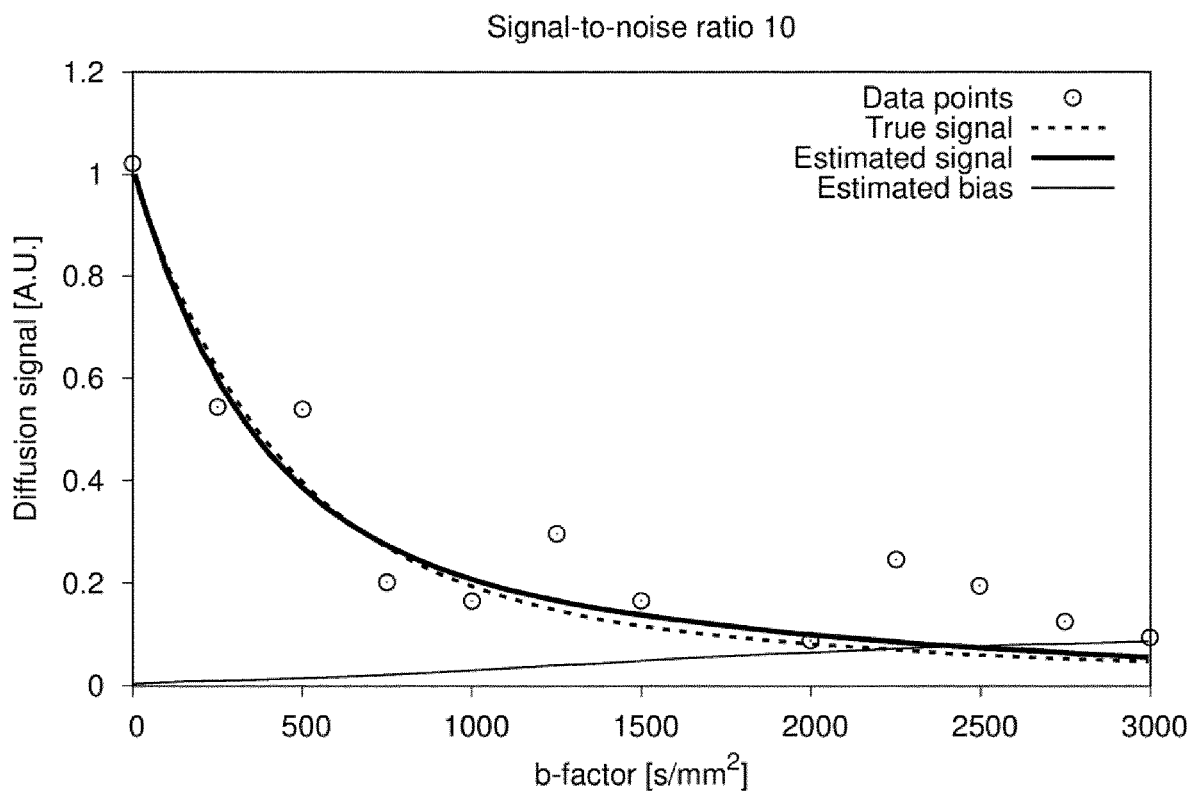
FIG. 10 is an illustrative graphical representation of simulated data for a b-factor range of 0 to 3000 sec/mm² and the result of using the method described herein to infer bias-free signal decay and bias.

FIG. 10 shows simulated signal decay with a signal-to-noise ratio of 10 at the lowest assumed b-factor. The magnitude of simulated complex signals at 13 b-factors between 0 and 3000 s/mm$^2$ was processed with the proposed method to estimate bias and true signal decay. As can be appreciated in the graph, true signal and estimated true signal decay match closely, supporting the notion that the proposed process is effective.

Figure 11A:
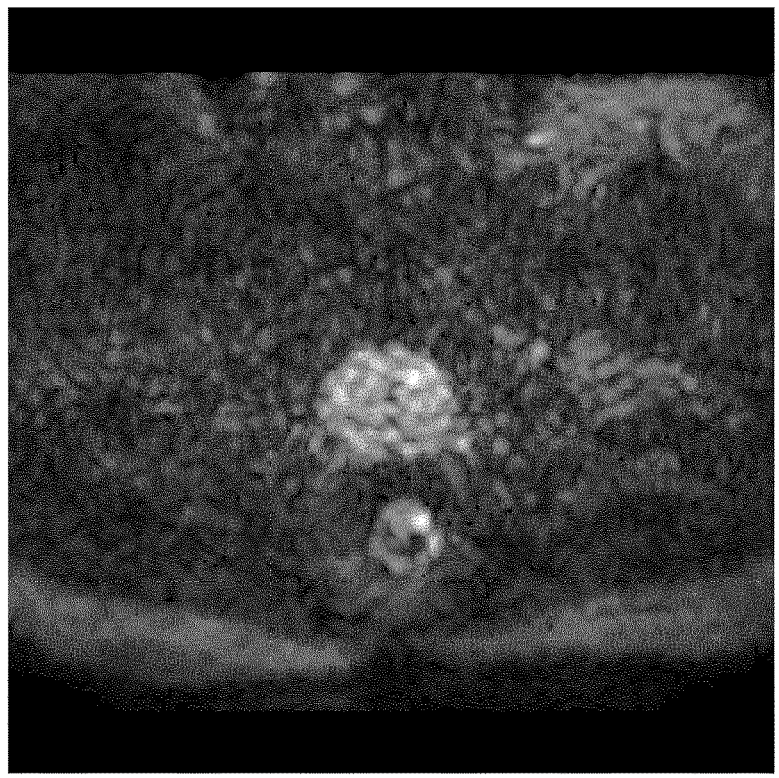
FIGS. 11A and 11B are illustrative graphical representations of geometrically averaged raw data of three diffusion-encoding directions obtained with the preferred imaging protocol at b-factors 1500 sec/mm² (FIG. 11A) and 3000 sec/mm² (FIG. 11B)
Figure 11B:
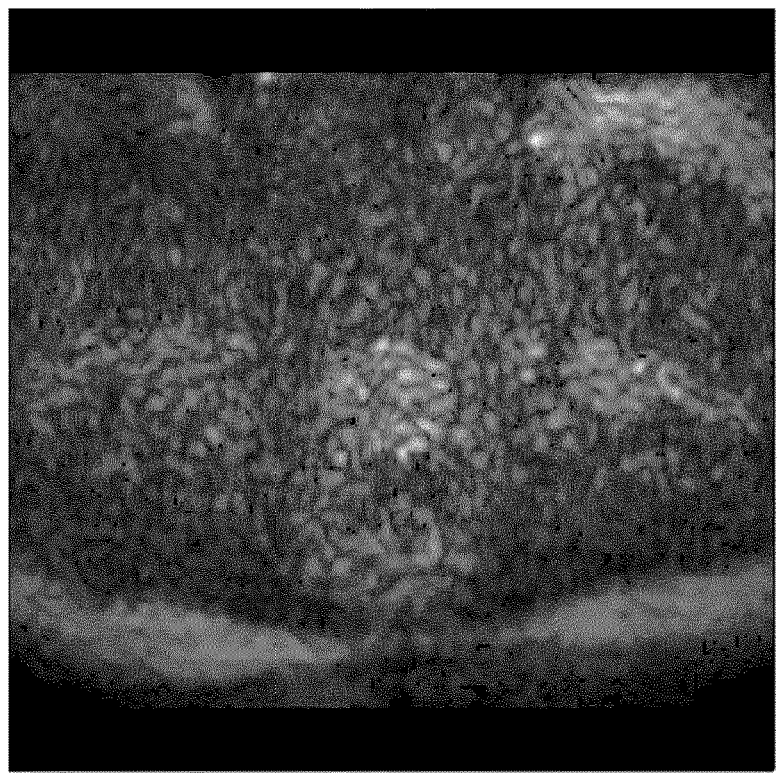
Figure 12A:
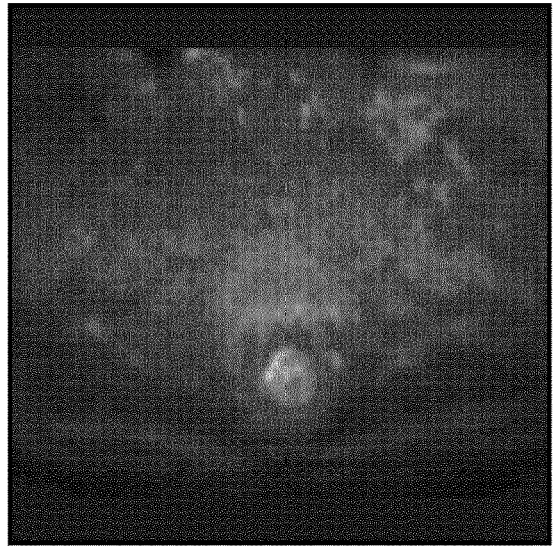
FIGS. 12A-D are illustrative comparisons of diffusion encoding direction averaged $\sigma_g$ maps obtained with the method described herein using the bi-exponential model (FIG. 12A), the gamma distribution related model (FIG. 12B) and the kurtosis model without (FIG. 12C) and with (FIG. 12D) spatial low pass filtering.
Figure 12B:
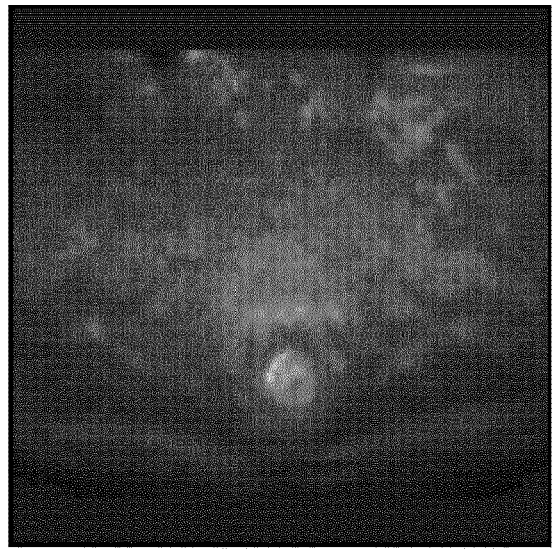
Figure 12C:
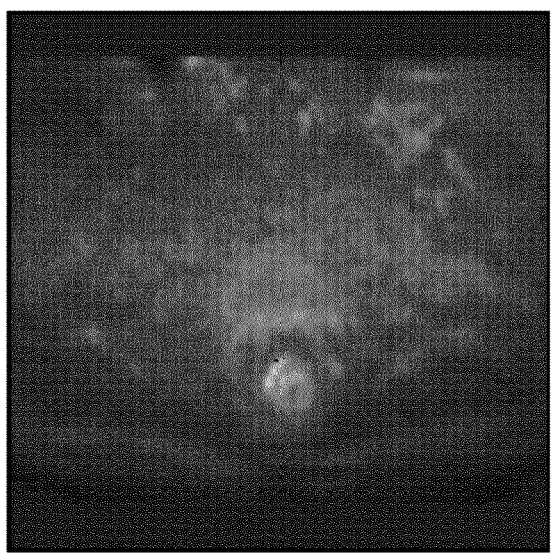
Figure 12D:
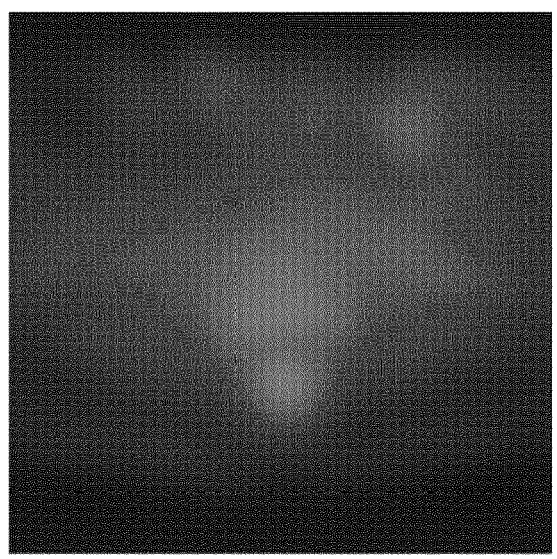

FIGS. 11A and 11B show directionally averaged signals of a prostate scan with an external coil array at b-factors 1500 and 3000 sec/mm$^2$, respectively. The overall inferior signal to noise ratio, particularly at a b-factor of 3000 sec/mm$^2$ can readily be appreciated. In the center of the image, a normal prostate, without any obvious high intensity cancer lesion, is clearly visible. The same data used to generate FIGS. 11A and 11B was used to evaluate the new method. To avoid any perfusion effects, which could be detrimental to finding the true tissue diffusion signal decay, only b-factor signals down to the second-lowest level, i.e., 150 s/mm$^2$, were included. FIGS. 12A-C show resulting noise maps after averaging the noise measured along three diffusion direction directions. Such maps were obtained with the bi-exponential model function (FIG. 12A), the gamma distribution related model function (FIG. 12B), and the kurtosis model function truncated to the second order polynomial (FIG. 12C). The similarity of these maps attests to the assumption that observed residuals are primarily noise related, rather than model function related. Finally, FIG. 12D shows a low pass filtered version of FIG. 12C. The low spatial variability of these estimated noise maps are in good agreement with noise profiles that result with coil arrays and parallel acceleration, i.e, there is clear tendency for noise amplification in the central area that is farthest away from all coils (see Pruessmann K P, Weiger M, Scheidegger M B, and Boesiger P.; SENSE: Sensitivity Encoding for Fast MRI, *Magn Reson Med*, 42:952-62, 1999).

Figure 13A:
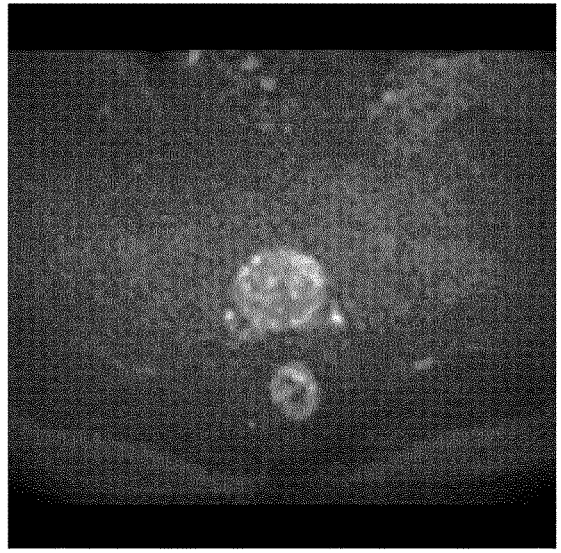
FIGS. 13A-D are illustrative comparisons of diffusion-weighted images at a b-factor of 1500 sec/mm² obtained with conventional averaging (FIG. 13A) and processed with the novel method using the bi-exponential model (FIG. 13B), the gamma distribution related model (FIG. 13C) and the kurtosis model (FIG. 13D)
Figure 13B:
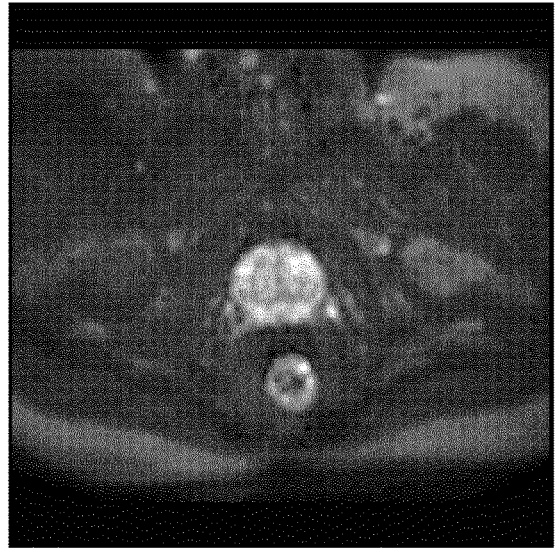
Figure 13C:
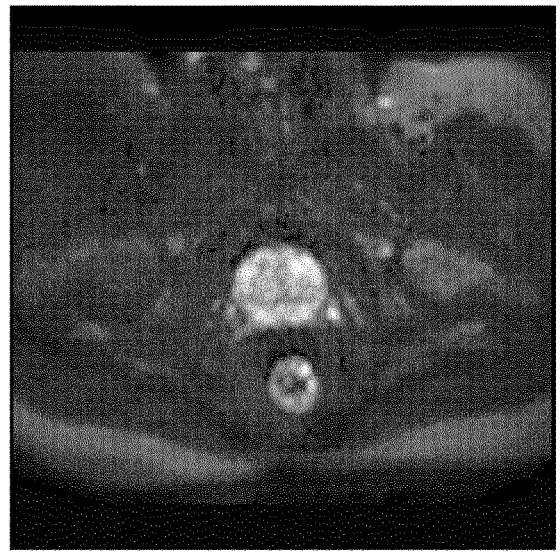
Figure 13D:
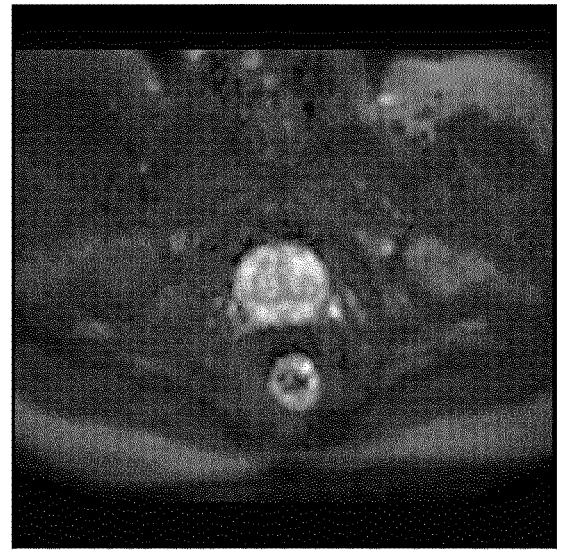

FIG. 13A shows the b-factor 1500 sec/mm$^2$ image obtained with the conventional scan protocol, i.e., after magnitude averaging signals from three directions and six repetitions of each direction. FIGS. 13B-C shows images of the geometric average of signals along three diffusion encoding directions obtained with the proposed distributed b-factor sampling and the new processing method for a b-factor of 1500 sec/mm$^2$ using the bi-exponential model function (FIG. 13B), the gamma distribution related model function (FIG. 13C), and the kurtosis model function truncated to the second order polynomial (FIG. 13D). The high detail visible on these images, particularly when compared to the image obtained with conventional imaging (FIG. 13A), underline the potential importance of the new method. The quality of these images in comparison to the image obtained with conventional averaging is particularly noteworthy in view of the substantially shorter duration of the experimental scan protocol.

Figure 14A:
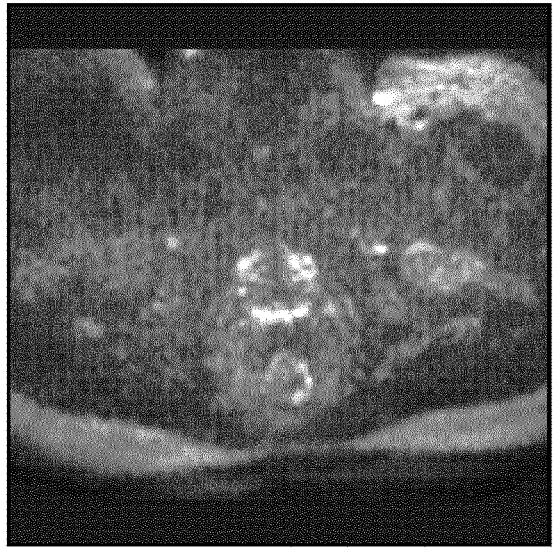
FIGS. 14A-D are illustrative comparisons of diffusion-weighted images at a b-factor of 3000 sec/mm² obtained with the novel method for a single diffusion-encoding direction with bias (FIG. 14A) and without bias (FIG. 14B), as well for three orthogonal diffusion-encoding directions geometrically averaged with bias (FIG. 14C) and without bias (FIG. 14D)
Figure 14B:
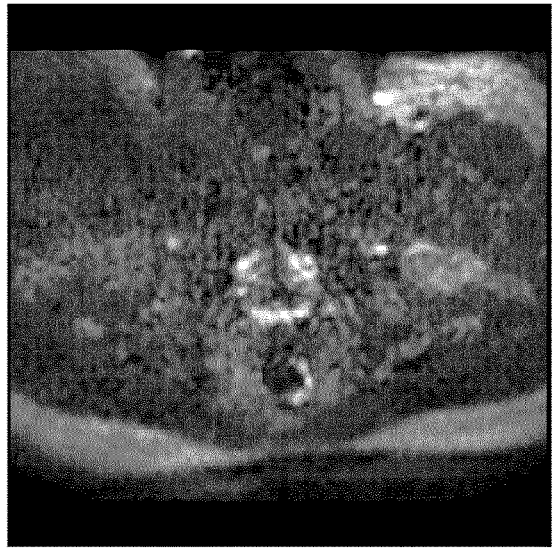
Figure 14C:
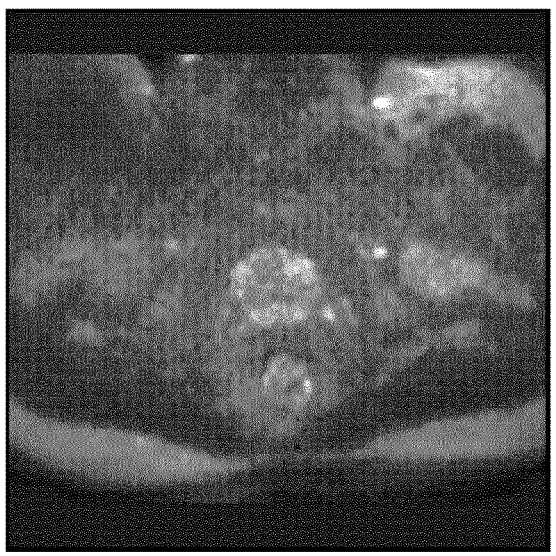
Figure 14D:
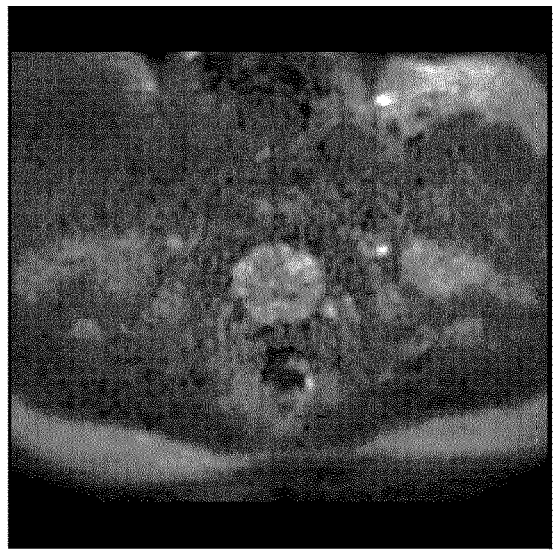
Figure 15:
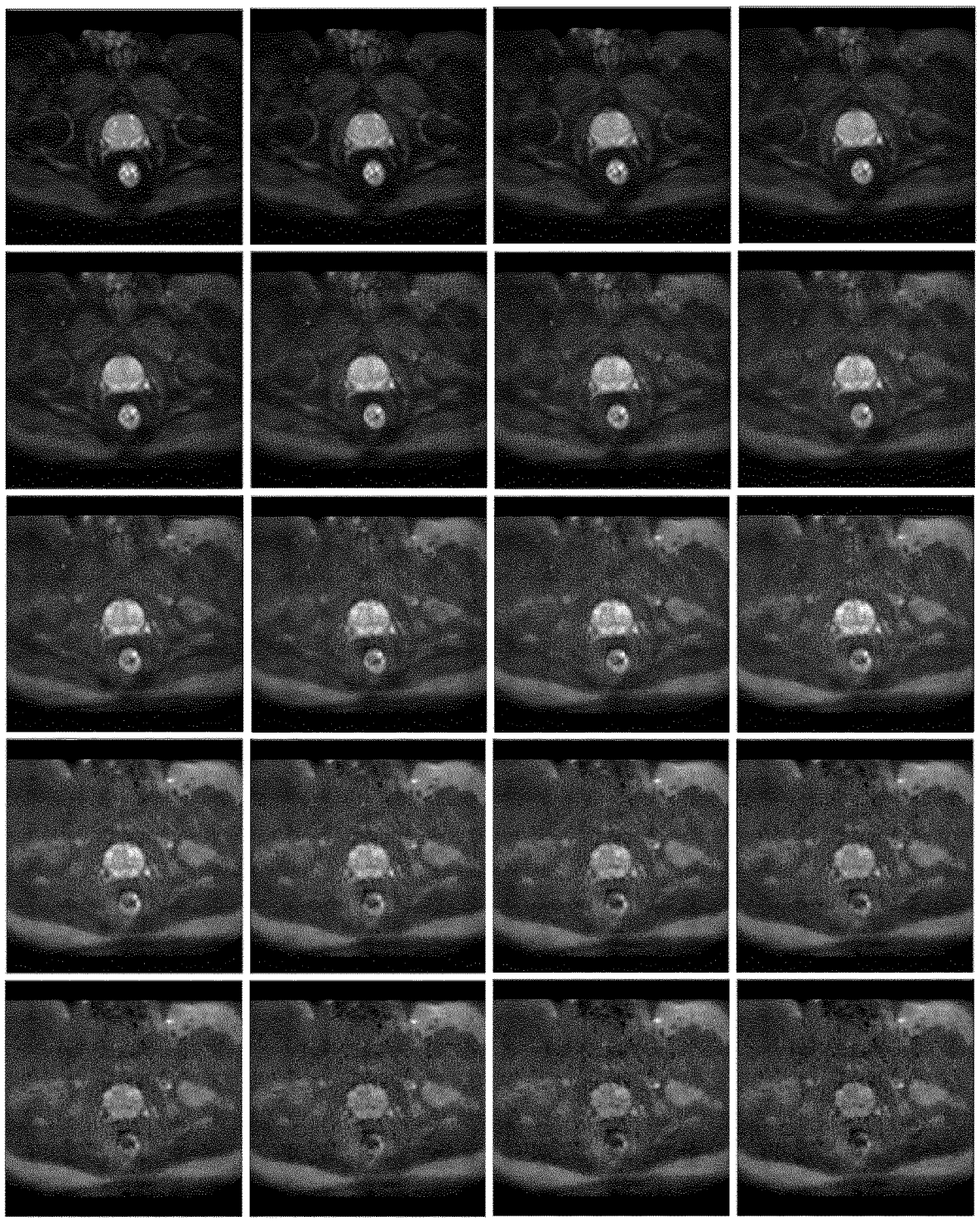
FIG. 15 is an illustrative graphical representation of an array of 20 images reconstructed with the new method proposed herein with b-factors equally spaced between 150 and 3000 sec/mm².

FIGS. 14A-D show additional images of the same reconstruction as shown in FIGS. 13B-C, but at the highest b-factor measured, i.e., 3000 sec/mm$^2$. Images shown in FIGS. 14A and B were reconstructed from a single superior-inferior diffusion encoding direction without removal of bias (FIG. 14A) and with removal of bias (FIG. 14B). The central region of the prostate shows clear signs of diffusion anisotropy related signal loss. Without bias removal this effect is clearly diminished. Images shown in FIGS. 14C and D were generated from the geometric average of the reconstructed signals of three diffusion encoding directions without removal of bias (FIG. 14C) and with removal of bias (FIG. 14D). At a diffusion-weighting level of 3000 sec/mm², a cancer lesion, if present, would impress as an easy distinguishable spot of high signal intensity. High quality images for the entire range of diffusion-weightings employed in the reconstruction with the new method, i.e., from 150 to 3000 sec/mm², sorted in ascending order from left to right and from top to bottom, are shown in FIG. 15.

Figure 16:
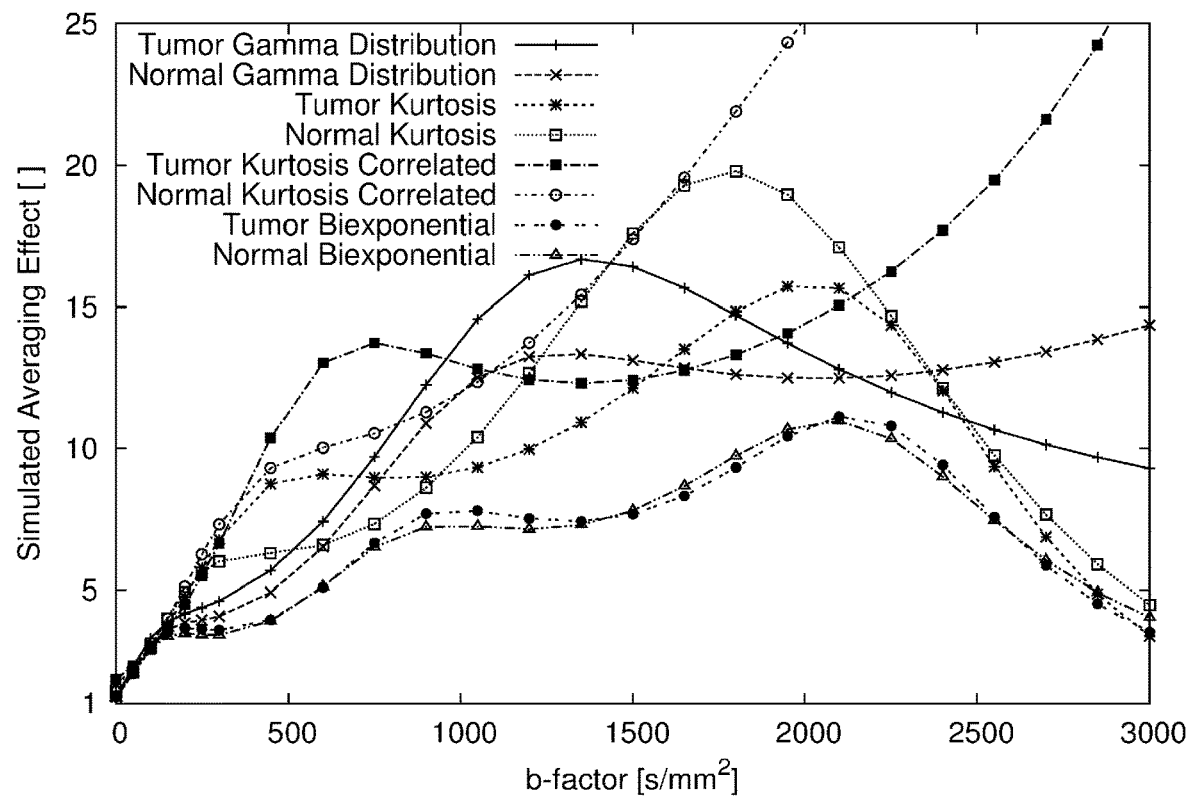
FIG. 16 is an illustrative graphical representation of a simulation to estimate the averaging effect of different fitting approaches.

To obtain the data shown in FIG. 16, a bi-exponential decay was simulated for normal tissue ($f$=0.8, $D_f$=2.2 μm²/ms, $D_s$=0.4 μm²/ms,) and tumor tissue ($f$=0.6, $D_f$=2.2 μm²/ms, $D_s$=0.2 μm²/ms). Noise was added to the decay signal in 10000 realizations and for each realization a gamma distribution related decay model, a kurtosis model, a correlated kurtosis model as proposed in this application and a bi-exponential model was fitted to the data. The standard deviation of the differences between fitted signals and the noise-free signal relative to noise was used to estimate the averaging effect. The lowest averaging effect is seen for low b-factors. The averaging effect, as might be expected, increases with decreasing number of model parameters.

Figure 17:
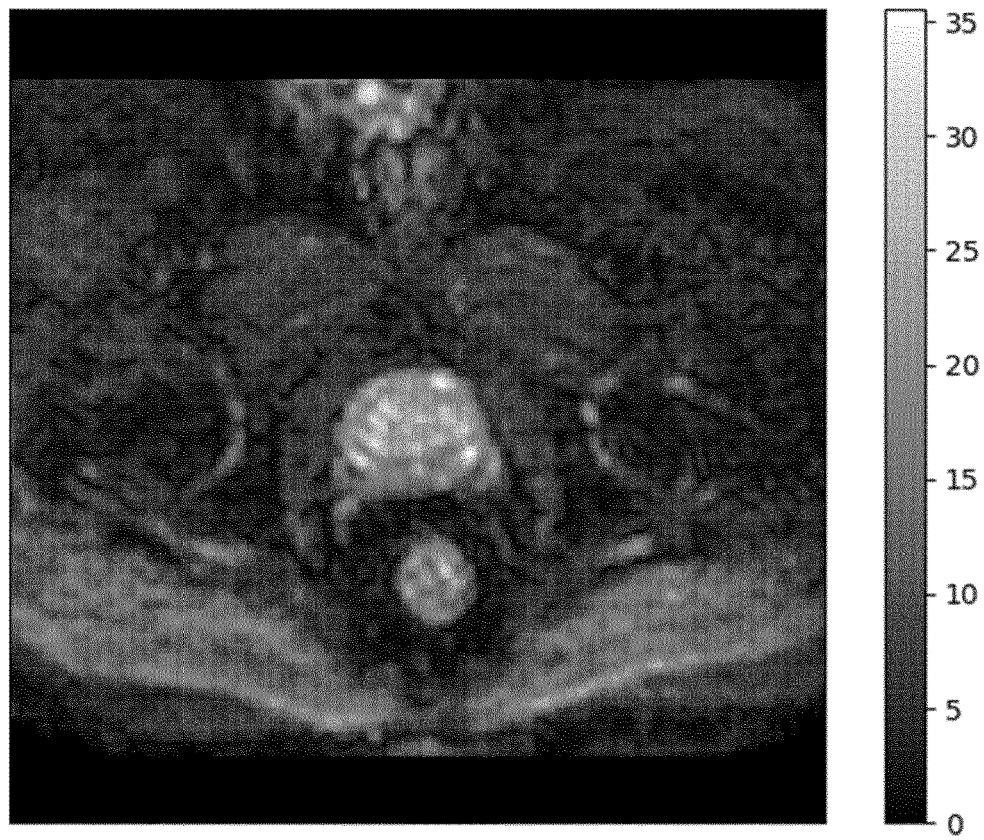
FIG. 17 is an illustrative graphical representation of a computed signal-to-noise ratio map together with a scale of absolute signal-to-noise ratio values for a single diffusion-encoding direction and a b-factor of 0.

Finally, FIG. 17 shows a synthesized map of signal-to-noise ratio for a single-direction measurement. With the help of the scale that shows absolute signal-to-noise ratio values, it can be concluded that for this experimental setup signal-to-noise ratios in the prostate reach levels between 20 and 30, and in some areas of the prostate peripheral zone as low as 15 or lower.

Figure 18A:
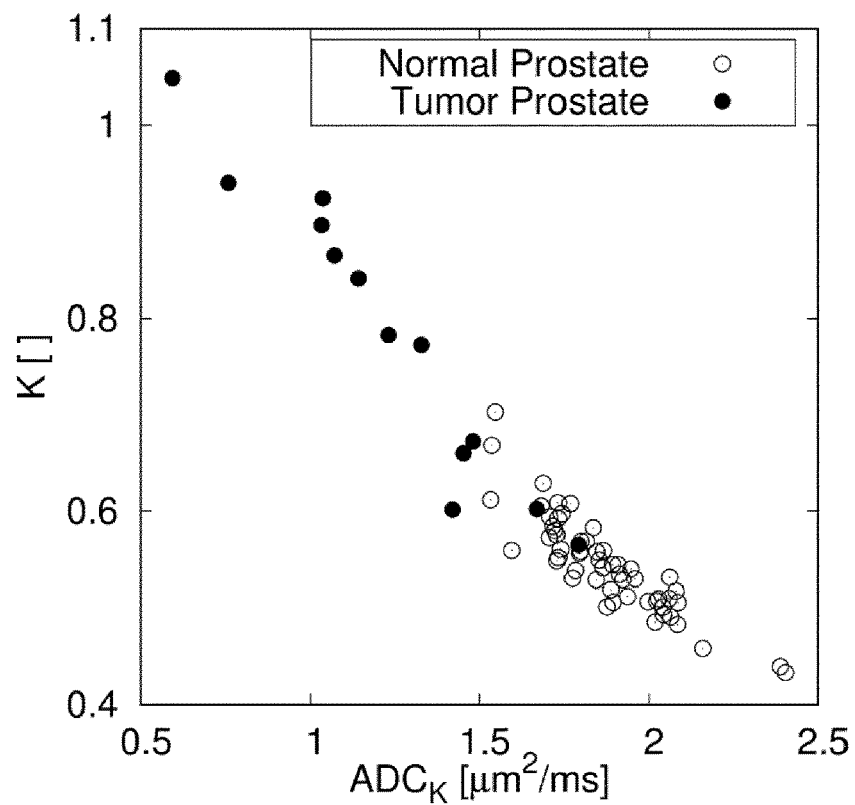
FIGS. 18A and 18B are illustrative graphical representations of kurtosis parameters K vs. $ADC_K$ for region of interest data measured in prostate (FIG. 18A) and pixel data measured in prostate and normal brain (FIG. 18B)
Figure 18B:
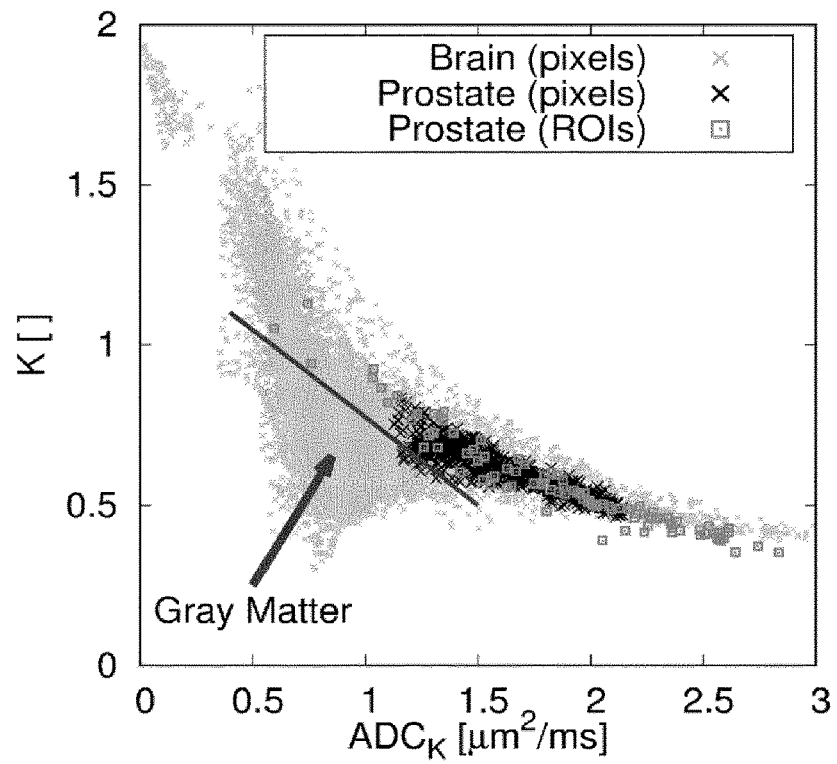
Figure 19:
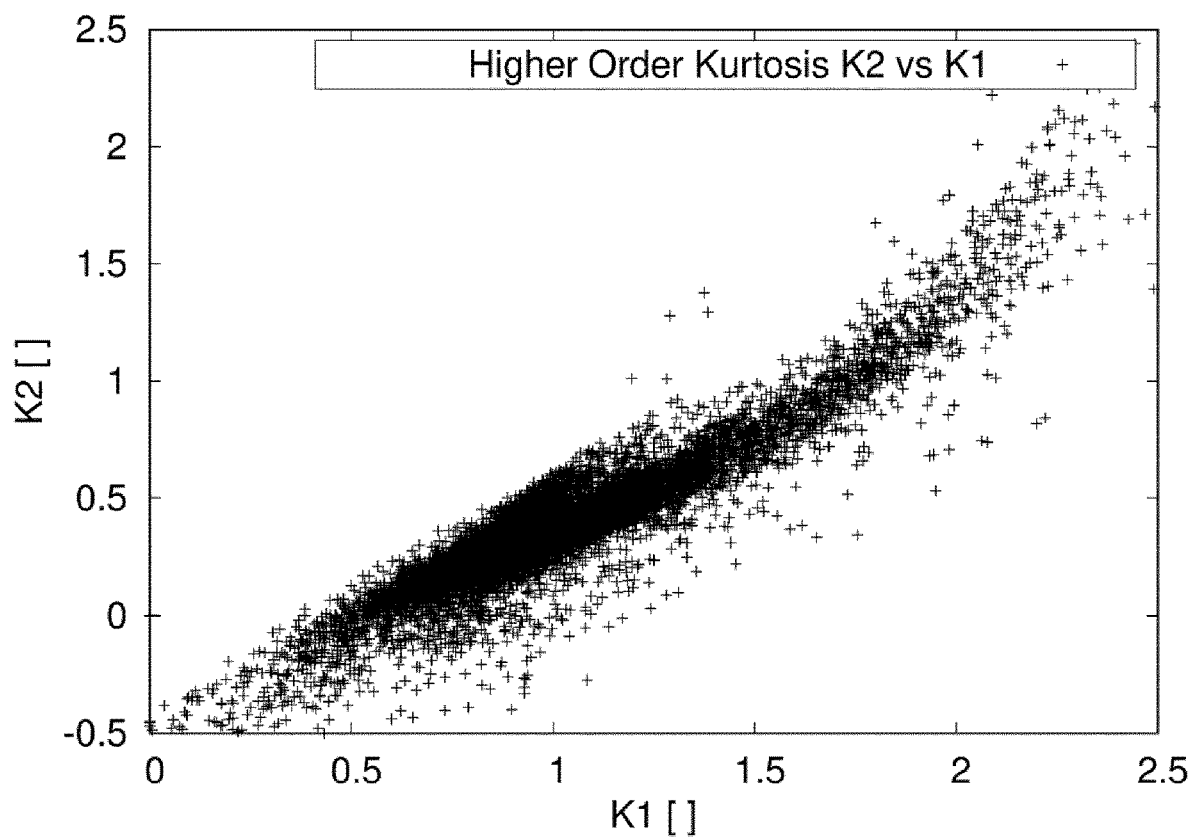
FIG. 19 is an illustrative graphical representation of kurtosis parameters $K_2$ vs. $K_1$ for pixel data measured in normal brain.

The following figures are based on data with exquisitely high signal-to-noise ratios of 100:1 and higher. These high signal-noise-ratios are the result of using large voxels and in the case of the prostate data, a small coil next to the tissue of interest. These high signal-to-noise ratios are believed to be helpful to best reflect the observed correlation between $ADC_K$ and K, $K_1$ and $K_2$ respectively. FIG. 18A shows a scatter plot of K vs. $ADC_K$ measured in 55 patients for regions of interest of normal prostate and prostate cancer lesions. For this data a high correlation coefficient $r^2$=0.92 can be determined (see Langkilde F, Kobus T, Fedorov A, Dunne R, Tempany C, Mulkern R V, and Maier S E.; Evaluation of Fitting Models for Prostate Tissue Characterization Using Extended-Range b-Factor Diffusion-Weighted Imaging, *Magn Reson Med.* 79:2346-2358, 2018). Meanwhile, FIG. 18B shows the same data, but now together with prostate pixel data of an individual patient and brain data of one normal subject. Except for pixels that can be attributed to gray matter, the parameters K vs. $ADC_K$ appear to exhibit a strong correlation. Finally, to obtain the data shown in FIG. 19, brain diffusion signals were processed with a kurtosis fit truncated to the third order polynomial. Evidently, there is a significant correlation between $K_1$ and $K_2$.

Figure 20A:
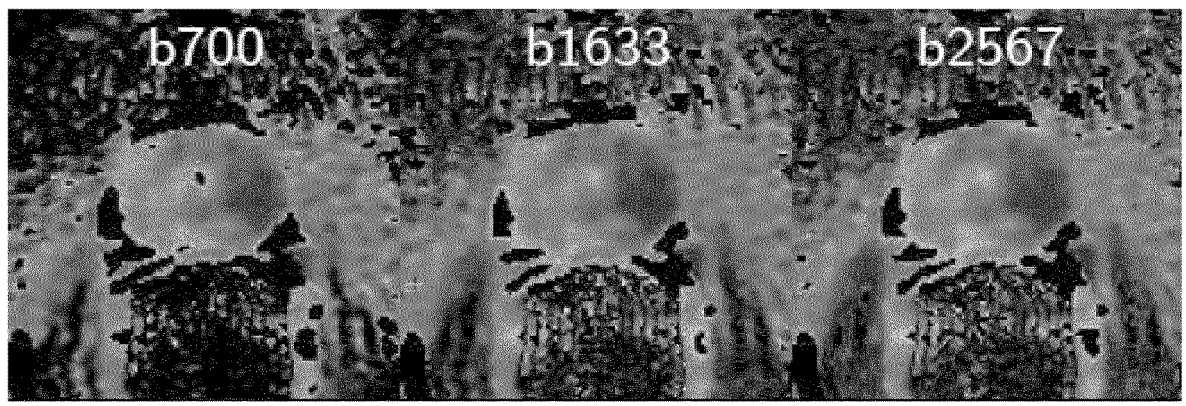
FIG. 20A-C are illustrative graphical representations of $ADC_K$ maps obtained with different ranges of b-factors (FIG. 20A) and diffusion-weighted images that were either measured, extrapolated with the proposed kurtosis model with assumed correlation between K and $ADC_K$, or extrapolated with a basic mono-exponential model for b=1633 sec/mm2 (FIG. 20B) and b=2567 sec/mm2 (FIG. 20C).
Figure 20B:
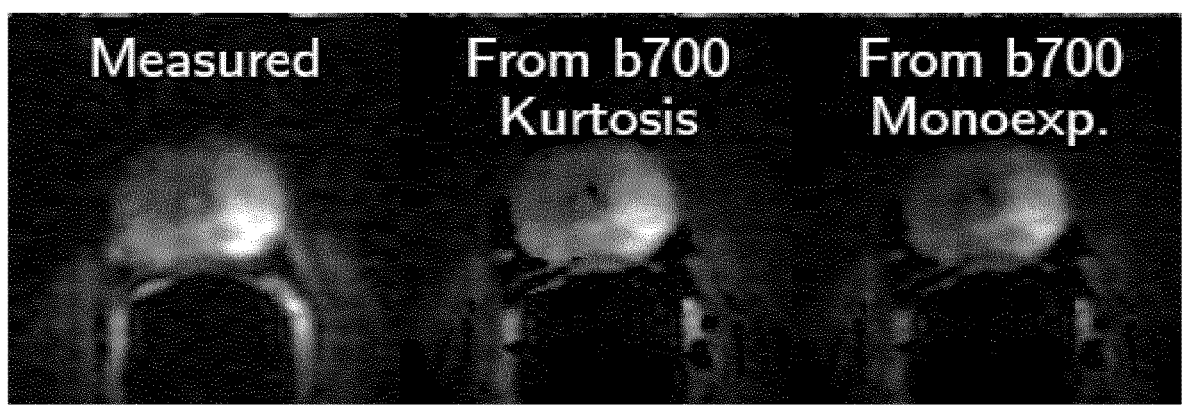
Figure 20C:
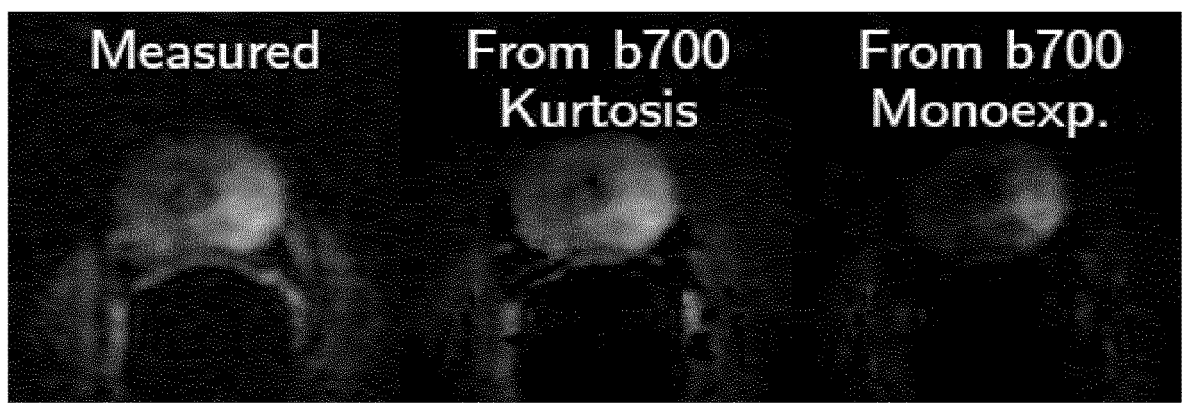

FIGS. 20A-C demonstrate the application of the novel kurtosis model fitting method based on a predetermined correlation between $ADC_K$ and K. Subsets of signal decay data were generated with a maximum b-factor of 700 sec/mm², 1633 sec/mm², and 2567 sec/mm² with 4, 8, and 12 b-factors, respectively. Based on the data shown in FIGS. 18A and B, a suitable second order polynomial function was determined to describe the parameter K as a function of the independent variable $ADC_K$. FIG. 20A shows nearly identical $ADC_K$ maps generated with the three data subsets using kurtosis fits, where K follows the predetermined polynomial function of $ADC_K$. In FIGS. 20B and C, true measured signals at b-factors 1633 sec/mm² (FIG. 20B) and 2567 sec/mm² (FIG. 20C) are compared to signals extrapolated from the data set with a maximum b-factor of 700 sec/mm² using the novel kurtosis fitting method and mono-exponential fitting. The images shown confirm the well-known inadequacy of mono-exponential analysis for extrapolating and describing diffusion at higher b-factors and the high potential the proposed method has to achieve exactly this goal.

Having thus described a preferred embodiment of the invention and an example indicative of its significance in the art, numerous modifications, alterations, variations, changes and the like will occur to those skilled in the art. For example, various other non-mono-exponential functions and close representations may occur to those skilled in the art within the scope of this invention in its broadest aspects. Accordingly, it is to be understood that the foregoing specification is to be understood as being illustrative only, and the scope of the invention is intended to be limited only by the terms of the appended claims.

The invention claimed is:

1. A method for highly reliable non-mono-exponential fitting of diffusion-weighted images, said method comprising the steps of:
   a) providing a magnetic resonance imaging apparatus capable of operation at diffusion encoding levels (b-factors) within a range ranging at least between an upper and a lower limit;
   b) acquiring a set of magnitude signal decays from a patient using said magnetic resonance imaging apparatus at each of a selected plurality of encoding levels distributed across the range of b-factors within its capability, each said set of signal decays being representative of an image of a preselected cross-section of the patient, and each said signal decay of each said set corresponding to a pixel of its associated image;
   c) processing said acquired or bias-corrected signal decays on a pixel by pixel basis to obtain the best possible fit between them and a non-mono-exponential equation wherein a non-linear least-squares method is used to obtain a fit,
   wherein the processing of said acquired or bias-corrected signal decays on a pixel by pixel basis in step 1c) is made to obtain the best possible fit between them and a non-mono-exponential equation of the form:

$$S(b) = S_0 \exp\left(-b \cdot ADC_K + b^2 \cdot ADC_K^2 \cdot \frac{K_1}{6} - b^3 \cdot ADC_K^3 \cdot \frac{K_2^2}{27}\right)$$

wherein, in this equation, $S_0$ is a constant that depends on constant values associated with (a) the magnetic imaging apparatus, (b) the spin-spin relaxation time T2, (c) the spin lattice relaxation time T1, and (d) the spin density ρ,
   wherein b is the diffusion encoding level, and
   wherein $ADC_K$ is a parameter for the apparent kurtosis diffusion coefficient, and
   wherein, $K_1$ is a parameter for the excess kurtosis, and
   wherein, $K_2$ is a second parameter for the excess kurtosis, and
   wherein $K_1$ and $K_2$ are expressed as predefined functions of $ADC_K$.

2. The method of claim 1, wherein said lower limit is below 500 sec/mm².

3. The method of claim 1, wherein said lower limit is below 300 sec/mm².

4. The method of claim 1, wherein said lower limit is below 150 sec/mm².

5. The method of claim 1, wherein said upper limit is above 2000 sec/mm².

6. The method of claim 1, wherein said upper limit is above 3000 sec/mm².

7. The method of claim 1, wherein said upper limit is about 5000 sec/mm² or higher.

8. The method according to claim 1, further using the method to compute images with signal values between sampled values and outside the acquired range.

9. The method according to claim 1, wherein results obtained are displayed such that a zero value is displayed as a black pixel, and the larger the value the brighter the display of the associated pixel becomes.

10. An apparatus for highly reliable non-mono-exponential fitting of diffusion-weighted images, said apparatus comprising a controller arranged to:
   a) receive a set of magnitude signal decays from a patient obtained from a magnetic resonance imaging apparatus at each of a selected plurality of encoding levels distributed across a range of b-factors within its capability, each said set of signal decays being representative of an image of a preselected cross-section of the patient, and each said signal decay of each said set corresponding to a pixel of its associated image;
   b) wherein said range of b-factors ranges at least between an upper and a lower limit; and
   c) processing said acquired or bias-corrected signal decays on a pixel by pixel basis to obtain the best possible fit between them and a non-mono-exponential equation, wherein a non-linear least-squares method is used to obtain a fit.

11. The apparatus of claim 10, wherein said lower limit is below 500 sec/mm².

12. The apparatus of claim 10, wherein said lower limit is below 300 sec/mm².

13. The apparatus of claim 10, wherein said lower limit is below 150 sec/mm².

14. The apparatus of claim 10, wherein said upper limit is above 2000 sec/mm².

15. The apparatus of claim 10, wherein said upper limit is above 3000 sec/mm².

16. The apparatus of claim 10, wherein said upper limit is about 5000 sec/mm² or higher.

17. A method for highly reliable non-mono-exponential fitting of diffusion-weighted images, said method comprising the steps of:
   a) providing a magnetic resonance imaging apparatus capable of operation at diffusion encoding levels (b-factors) within a range ranging at least between an upper and a lower limit;
   b) acquiring a set of magnitude signal decays from a patient using said magnetic resonance imaging apparatus at each of a selected plurality of encoding levels distributed across the range of b-factors within its capability, each said set of signal decays being representative of an image of a preselected cross-section of the patient, and each said signal decay of each said set corresponding to a pixel of its associated image;
   c) processing said acquired or bias-corrected signal decays on a pixel by pixel basis to obtain the best possible fit between them and a non-mono-exponential equation wherein a non-linear least-squares method is used to obtain a fit, wherein said lower limit is below 500 sec/mm².

* * * * *